(12) United States Patent
Tokhtuev et al.

(10) Patent No.: US 9,696,261 B2
(45) Date of Patent: Jul. 4, 2017

(54) MULTI-CHANNEL DEVICE AND METHOD FOR MEASURING OPTICAL PROPERTIES OF A LIQUID

(75) Inventors: Eugene Tokhtuev, Duluth, MN (US); Christopher J. Owen, Duluth, MN (US); Viktor Slobodyan, Duluth, MN (US); William M. Christensen, Hibbing, MN (US); Paul Schilling, Duluth, MN (US); Joseph Phillip Erickson, Cloquet, MN (US)

(73) Assignee: Ecolab USA Inc., St. Paul, MN (US)

( * ) Notice: Subject to any disclaimer, the term of this patent is extended or adjusted under 35 U.S.C. 154(b) by 1269 days.

(21) Appl. No.: 12/247,767

(22) Filed: Oct. 8, 2008

(65) Prior Publication Data

US 2009/0098022 A1  Apr. 16, 2009

Related U.S. Application Data

(60) Provisional application No. 60/998,639, filed on Oct. 12, 2007.

(51) Int. Cl.
| | |
|---|---|
| *G01N 21/00* | (2006.01) |
| *G01N 21/01* | (2006.01) |
| *G01N 21/25* | (2006.01) |
| *G01N 21/78* | (2006.01) |
| *G01N 21/27* | (2006.01) |
| *G01N 21/51* | (2006.01) |
| *G01N 33/18* | (2006.01) |

(52) U.S. Cl.
CPC .......... *G01N 21/78* (2013.01); *G01N 21/274* (2013.01); *G01N 21/51* (2013.01); *G01N 33/18* (2013.01)

(58) Field of Classification Search
CPC ...... G01N 21/78; G01N 21/274; G01N 21/51; G01N 33/18
USPC .................... 422/82.05–82.11, 68.1
See application file for complete search history.

(56) References Cited

U.S. PATENT DOCUMENTS

| | | | | |
|---|---|---|---|---|
| 3,523,738 | A | * | 8/1970 | Chisholm ..................... 356/440 |
| 4,332,769 | A | | 6/1982 | Rampy et al. |
| 4,537,747 | A | | 8/1985 | Castaneda |
| 4,596,780 | A | | 6/1986 | Castaneda |
| 4,876,068 | A | | 10/1989 | Castaneda |
| 4,920,057 | A | | 4/1990 | Castaneda |
| 5,013,155 | A | | 5/1991 | Rybak |

(Continued)

OTHER PUBLICATIONS

Suzuki, Yasutada, et al. "A simple and portable colorimeter using a red-green-blue light-emitting diode and its application to the on-site determination of nitrite and iron in river-water." Analytical sciences 20.6 (2004): 975-977.*

(Continued)

*Primary Examiner* — Lyle Alexander
*Assistant Examiner* — Robert Eom
(74) *Attorney, Agent, or Firm* — Shumaker & Sieffert, P.A.

(57) ABSTRACT

A multi-channel device includes up to three channels for optical testing of liquid samples. The liquid sample(s) may include surface water, drinking water, processed water or the like. The multi-channel device may include a turbidity channel and a color channel that measure turbidity and color, respectively, of a liquid sample using spectrographic analysis. The multi-channel device may also include a colorimetric channel that measures the concentration of various analytes in a liquid sample, such as free chlorine, total chlorine, copper and phosphate.

10 Claims, 16 Drawing Sheets

(56) References Cited

U.S. PATENT DOCUMENTS

| | | | |
|---|---|---|---|
| D327,027 S | 6/1992 | Chipley | |
| 5,423,440 A | 6/1995 | Castaneda et al. | |
| 5,434,664 A * | 7/1995 | Sapp | 356/244 |
| 5,646,736 A | 7/1997 | Rampy et al. | |
| 5,895,920 A * | 4/1999 | Carlsson | 250/461.1 |
| 6,686,691 B1 * | 2/2004 | Mueller et al. | 313/503 |
| 7,777,877 B2 * | 8/2010 | Walker et al. | 356/246 |
| 2003/0058450 A1 * | 3/2003 | Mosley et al. | 356/436 |
| 2006/0198761 A1 * | 9/2006 | Tokhtuev | G01N 21/251 422/82.05 |

OTHER PUBLICATIONS www.hamamatsu.com, Si photodiodes S2386 series datasheet, p. 1-4.*

Machery-Nagel Bioanalysis Catalog 2006, cover page and pp. 60-62.

"V-2000 Multi-analyte Photometer", CHEMetrics for good measure, http://www.chemetrics.com/v2000.htm, printed Jan. 4, 2009, 3 pgs.

"Operator's Manual V2000 Photometer", CHEMetrics, Inc. Dec. 2008, www.chemetrics.com, (24 pgs).

* cited by examiner

MULTI-CHANNEL DEVICE AND METHOD FOR MEASURING OPTICAL PROPERTIES OF A LIQUID

CROSS-REFERENCE TO RELATED APPLICATION

This application claims the benefit of U.S. provisional Application Ser. No. 60/998,639 filed Oct. 12, 2007, the entire content of which is incorporated herein by reference.

TECHNICAL FIELD

The invention generally relates to a portable device for testing a liquid sample, and more particularly to a multi-channel device for optically testing of water samples.

BACKGROUND OF THE INVENTION

Water intended for human use and consumption should be free of harmful chemicals and disease-causing bacteria or other microorganisms. A chlorine gas or a chlorine solution is often added to water for disinfection and control of microorganisms. However, testing for residual chlorine concentration after water treatment should be done because chlorine is known to react with organic matter in the water to form trihalomethanes (THMs), a suspected carcinogen.

Free chlorine is defined as the concentration of residual chlorine in water present as dissolved gas (Cl2), hypochlorous acid (HOCl), and/or hypochlorite ion (OCl—). Combined chlorine is defined as the residual chlorine existing in water in chemical combination with ammonia or organic amines which can be found in natural or polluted waters. Total chlorine is the sum of free and combined chlorine.

Commercially available multi-parameter instruments for water analysis include, for example, the LaMotte TC-3000 Tri-Meter, which measures turbidity, color and chlorine, or Hanna Instruments C 114 Turbidity and Chlorine Meter, which measures turbidity and chlorine. For chlorine evaluation both of these instruments use colorimetric methods when specific chemicals that change their color in the presence of chlorine are added to a water sample. Chlorine concentration can then be evaluated by intensity of color produced in the sample. Colorimetric kits and methods are developed by several companies such as CHEMetrics, LaMotte, Hach, Hanna for many analytes. Colorimetric test kits including as a pre packed set of chemicals are available, for example, under the trade name VISOCOLOR® Test kit for water analysis (http://www.cscjp.co.jp/VISOCOLOR_e.pdf) which allows for evaluation of multiple parameters and components in water. Colorimetric kits are developed for visual evaluation and for use with different optical instruments, such as spectrophotometers and photometers. The photometer PF-11 (VISOCOLOR®) which is recommended for use with a VISOCOLOR®Test kit is a single beam filter photometer having a filter wheel with 6 colored glass filters and manual wavelength adjustment. It uses six wavelengths—380 nm, 405 nm, 470 nm, 520 nm, 605 nm and 720 nm from a tungsten lamp. The wavelengths are chosen to match absorbance peaks for specific colorimetric reactions.

Colorimetric test kits having self-filling reagent ampoules are available from CHEMetrics http://www.chemetrics.com/selffill.html) when company introduced the self-filling reagent ampoules. The CHEMetrics Model V-2000 photometer uses one of three light emitting diodes (LED) to measure the optical density of a test ampoule after the water sample is mixed with reagent producing a specific color reaction.

SUMMARY OF THE INVENTION

The present invention is a multi-channel device for optical testing of various properties of a liquid sample. The multi-channel device may measure turbidity and/or color of a liquid sample using spectroscopic analysis. The multi-channel device may also measure the concentration of various analytes in a liquid sample, such as free chlorine, total chlorine, copper, phosphate, fluoride, etc. using colorimetric analysis.

In one embodiment, the invention is directed to a system comprising a sample chamber that holds a liquid sample of which at least one analyte concentration is to be determined, a colorimetric channel that measures the analyte concentration of the liquid sample, wherein the colorimetric channel further includes, a multicolor light source that directs light of a first selected color range into the liquid sample, and a multicolor detector that detects light of a second selected color range that is different than the first selected color range transmitted through the liquid sample, and a controller that determines the analyte concentration of the liquid sample based on the detected light of the second color range.

In another embodiment, the invention is direct to an apparatus comprising a sample chamber sized to receive an ampoule containing a liquid sample of which at least one analyte concentration is to be determined, a colorimetric channel that measures the analyte concentration of the liquid sample, wherein the colorimetric channel further includes a multicolor light source that directs light of a first selected color range into the liquid sample, and a multicolor detector that detects light of a second selected color range that is different than the first selected color range transmitted through the liquid sample, and a controller that determines the analyte concentration of the liquid sample based on the detected light of the second color range, wherein the sample chamber contains water during determination of the analyte concentration.

In another embodiment, the invention is directed to a method selecting a dye standard for calibrating a colorimetric channel in a multi-channel device that measures concentration of an analyte in a liquid sample, preparing a plurality of dye standard samples having concentrations corresponding to an optical density range of interest, collecting optical density data for each of the plurality of dye standard samples, applying a linearization procedure to the optical density data to generate a linearized optical density curve, and applying a normalization coefficient to the linearized optical density curve to generate a normalized optical density curve such that a chosen concentration of the dye standard corresponds to a chosen optical density.

The details of one or more embodiments of the invention are set forth in the accompanying drawings and the description below. Other aspects of the invention will be apparent from the description and drawings, and from the claims.

DETAILED DESCRIPTION OF THE INVENTION

The invention generally relates to a multi-channel device for optical testing of liquid samples. The liquid sample(s) may include surface water, drinking water, processed water or the like. The multi-channel device may measure turbidity and/or color of a liquid sample using spectroscopic analysis. The multi-channel device may also measure the concentration of various analytes in a liquid sample, such as free chlorine, total chlorine, copper and phosphate using colorimetric analysis.

Figure 1:
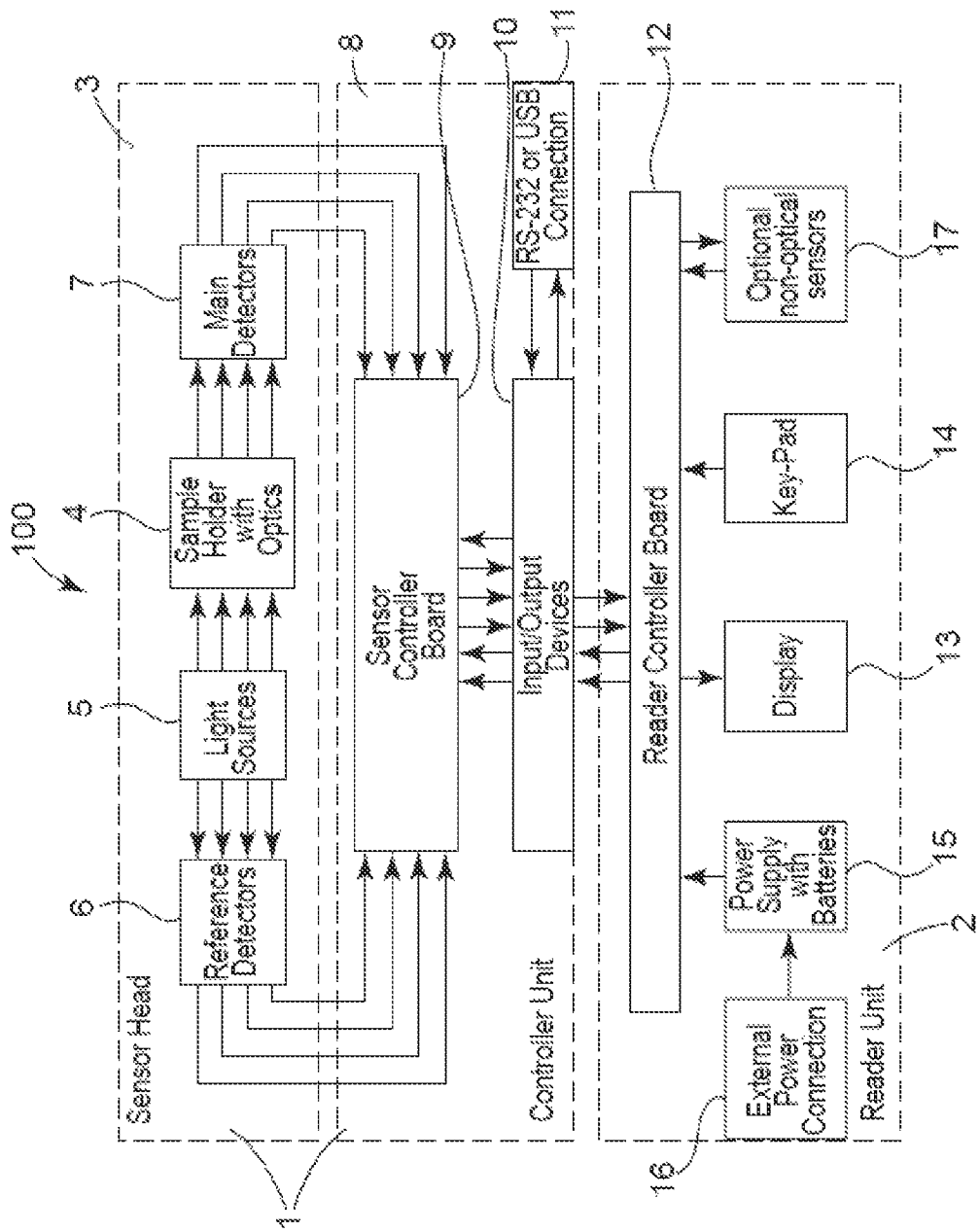
FIG. 1 shows a block diagram of an example multi-channel device.

FIG. 1 shows a block diagram of an example embodiment of a multi-channel device 100. The multi-channel device 100 includes a sensor unit 1 and a reader unit 2. Sensor unit 1 consists of a sensor head 3 having a sample holder 4, light sources 5, reference detectors 6, main detectors 7 and a controller unit 8. Controller unit 8 includes a sensor controller board 9, input/output devices 10 and a RS232 or USB connector 11. In the example multi-channel device 100, controller unit 8 is located inside of reader unit 2 and the sensor head 3 is located outside of reader unit 2. Reader unit 2 includes a reader controller board 12, a display 13, a keypad 14, a power supply 15 with an external power connector 16 and optional non-optical sensors 17.

Figure 2:
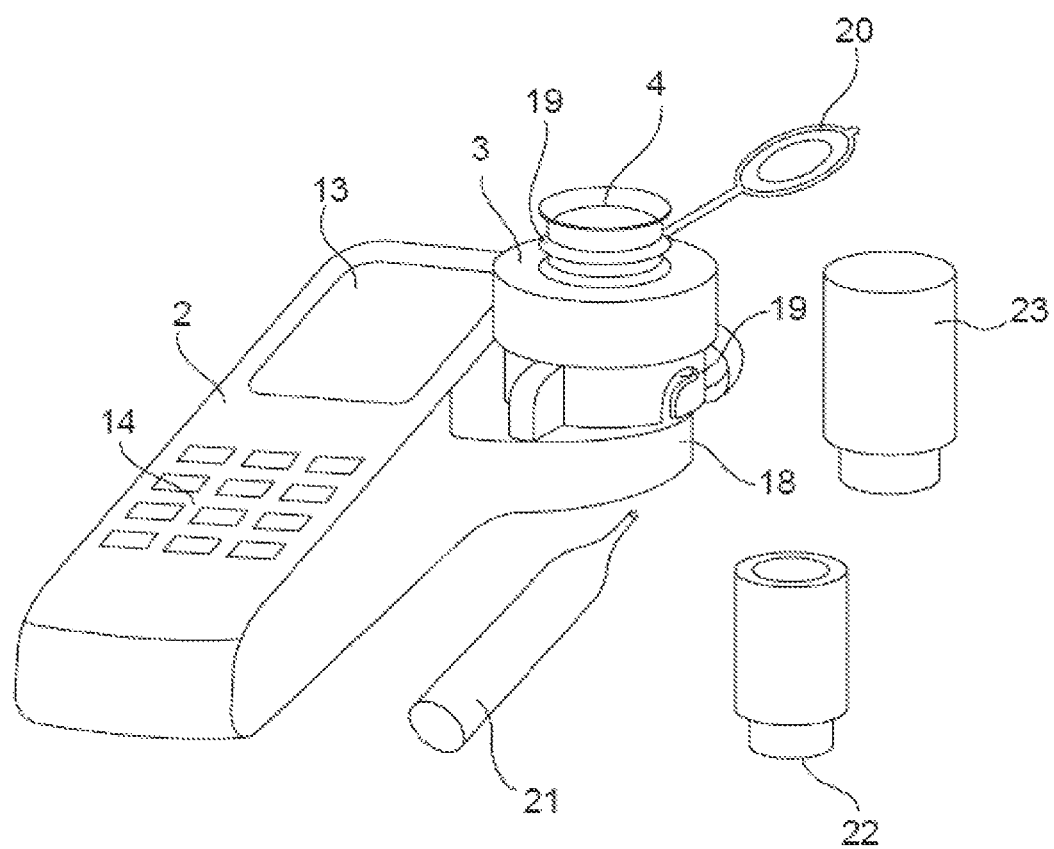
FIG. 2 shows a perspective view of the example multi-channel device in FIG. 1.

FIG. 2 shows a front perspective view of an example multi-channel device 100. Reader unit 2 includes display 13 and keypad 14 on the top part of the reader unit and an extended area on the side having a bayonet mount 18. Bayonet mount 18 includes bayonet pins to secure sensor head 3, which includes bayonet slits 19 at its lower part.

Multi-channel device 100 monitors optical properties of a liquid sample placed in a sample compartment (not shown in FIG. 2) of sample holder 4. For example, multi-channel device 100 may evaluate turbidity of the liquid sample, may evaluate color of the liquid sample and/or may measure concentration of multiple substances (analytes) present in the liquid sample using a colorimetric method.

To perform colorimetric measurements, a liquid sample may be mixed with a chemical compound and poured directly into the sample compartment of sample holder 4. An opaque lid 20 covers the sample holder 4 during measurements. In another example, a test ampoule 21 is vacuumed and pre-filled with a chemical compound. The chemical compound is chosen based upon the analyte in the sample to be measured. To measure analyte concentration(s) in the sample, test ampoule 21 containing the appropriate chemical compound is inverted and cracked in a volume of the sample. Atmospheric pressure pushes the liquid sample inside of test ampoule 21, thus mixing the liquid sample and the chemical compound to produce a colorimetric reaction inside of test ampoule 21. To analyze the sample, test ampoule 21 is placed inside of sample chamber 52. In one embodiment, water is added to sample chamber 52 before the test ampoule 21 is placed in the sample chamber 52. An ampoule holder 22 may also be placed at the top portion of sample holder 4. When an ampoule holder is used, test ampoule 21 with the liquid sample is placed inside of ampoule holder 22 and covered with an ampoule cover 23. More details concerning the evaluation of optical properties performed by multi-channel device 100 are described in greater detail herein below.

Figure 3:
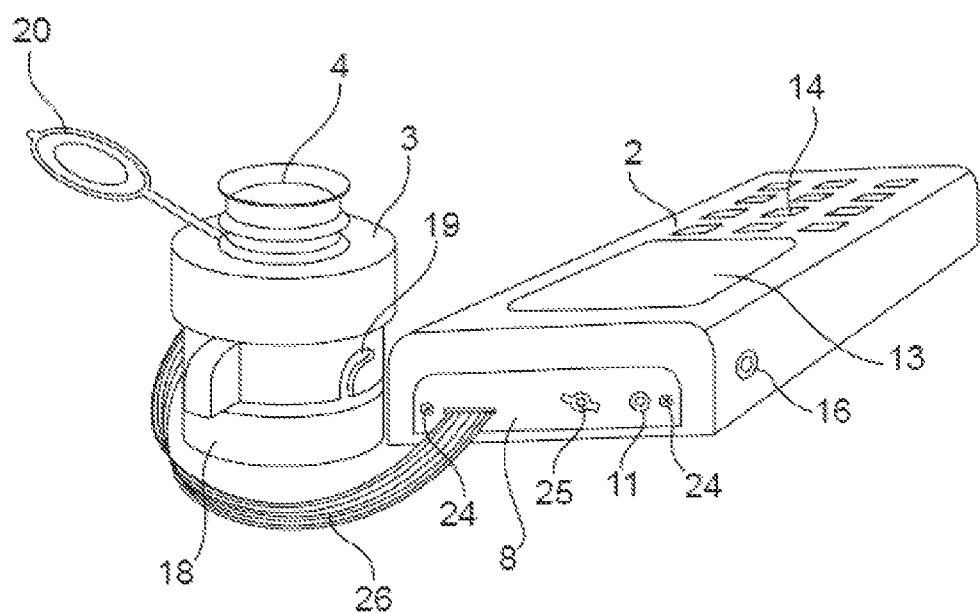
FIG. 3 shows a perspective view of the example multi-channel device in FIG. 1 from the back.

FIG. 3 shows a back perspective view of an example multi-channel device 100. Controller unit 8 is inserted inside of the reader unit 2 and secured with screws 24. Controller unit 8 includes RS232 connector 11 which may be covered with a protective rubber plug 25 when not in use. Controller unit 8 is connected to the sensor head 3 with a flat cable 26.

Figure 4:
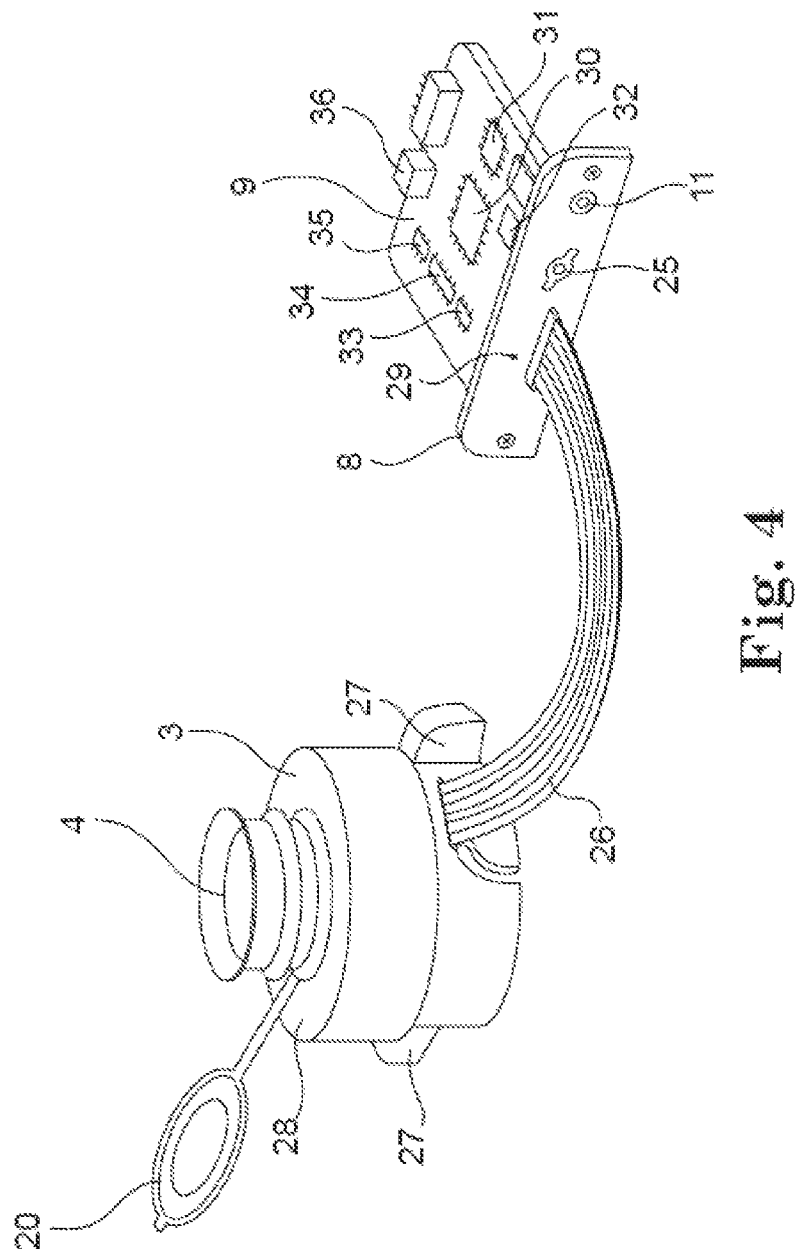
FIG. 4 shows a perspective view of an example sensor head and the controller unit disassembled from the reader.

FIG. 4 shows the sensor head 3 and the controller unit 8 separately from the reader unit. Sample holder 4 has two extended wings 27, which are added to make easier assembling and disassembling of sensor head 3 at bayonet mount 18 (shown in FIG. 2). An opaque cover 28 protects the optics and electronics mounted on the sample holder 4. Flat cable 26 may be hermetically sealed where it exits sample holder 4 and where it enters controller unit 8 through a slit in a mounting plate 29. Mounting plate 29 supports sensor controller board 9, which includes a processor 30, a memory 31, a RS-232 converter 32 and a settable voltage regulator 33. Settable voltage regulator 33 allows individually adjusted voltages to be set for each light source using two programmable potentiometers 34 and 35. Sensor controller board 9 receives external DC power (3.5V and 5 V) through a power connector 36. Processor 30 uses calibration data stored in memory 31. RS-232 converter 32 converts data from processor 30 to provide a standard RS-232 protocol. A connector 37 provides connection lines for $I^2C$ communication between sensor controller board 9 and reader controller board 12.

Figure 5:
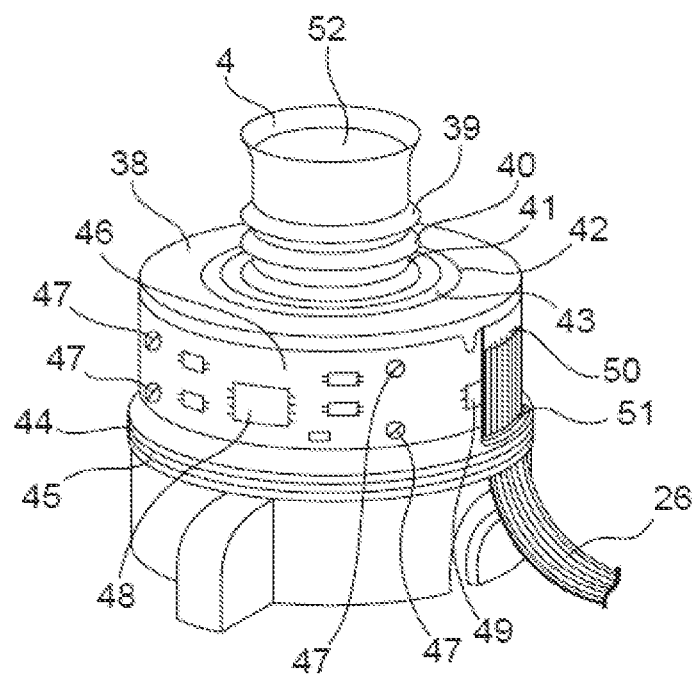
FIG. 5 shows a perspective view of an example sensor unit with the cover removed.

FIG. 5 shows an example sensor head 3 with cover 28 removed. Sample holder 4 further includes a sample holder body 38 having a snap rib 39 for securing cover 28, a groove 40 for a first o-ring 41, a groove 42 for a second o-ring 43 and a groove 44 for a third o-ring 45. A flexible board 46 (also referred to as a "flex board") is wrapped around sample holder body 38 and secured with mounting screws 47. Optoelectronic components such as light sources 5, reference detectors 6 and main detectors 7 are placed an inside surface (not shown in FIG. 5) of flex board 46. Some electronic components, such as an electronic chip 48 (first I/O expander), a temperature sensor 49, digital switches to control light sources are placed on the outside surface of the flexible board 46. Flat cable 26 is soldered to contact pads 50 at flex board 46. After flex board 46 is secured with screws 47 the cable 26 is fed through a slit 51 and then the slit 51 is filled with epoxy compound to seal a gap around flat cable 46. A sample compartment 52 is located in the center of sample holder 4. The sample compartment is a cavity for either direct placement of a liquid sample or placement of an ampoule containing the liquid sample.

Sample holder 4 includes three optical channels:

(1) a turbidity channel that measures turbidity using optical scattering and transmittance in a visible or infrared range of spectra;

(2) a color/scattered turbidity channel that measures color of a sample water using light transmittance in a visible or ultraviolet range of spectra; and (3) a colorimetric channel having a multicolor light emitting diode (LED) and a multicolor light detector.

Figure 7:
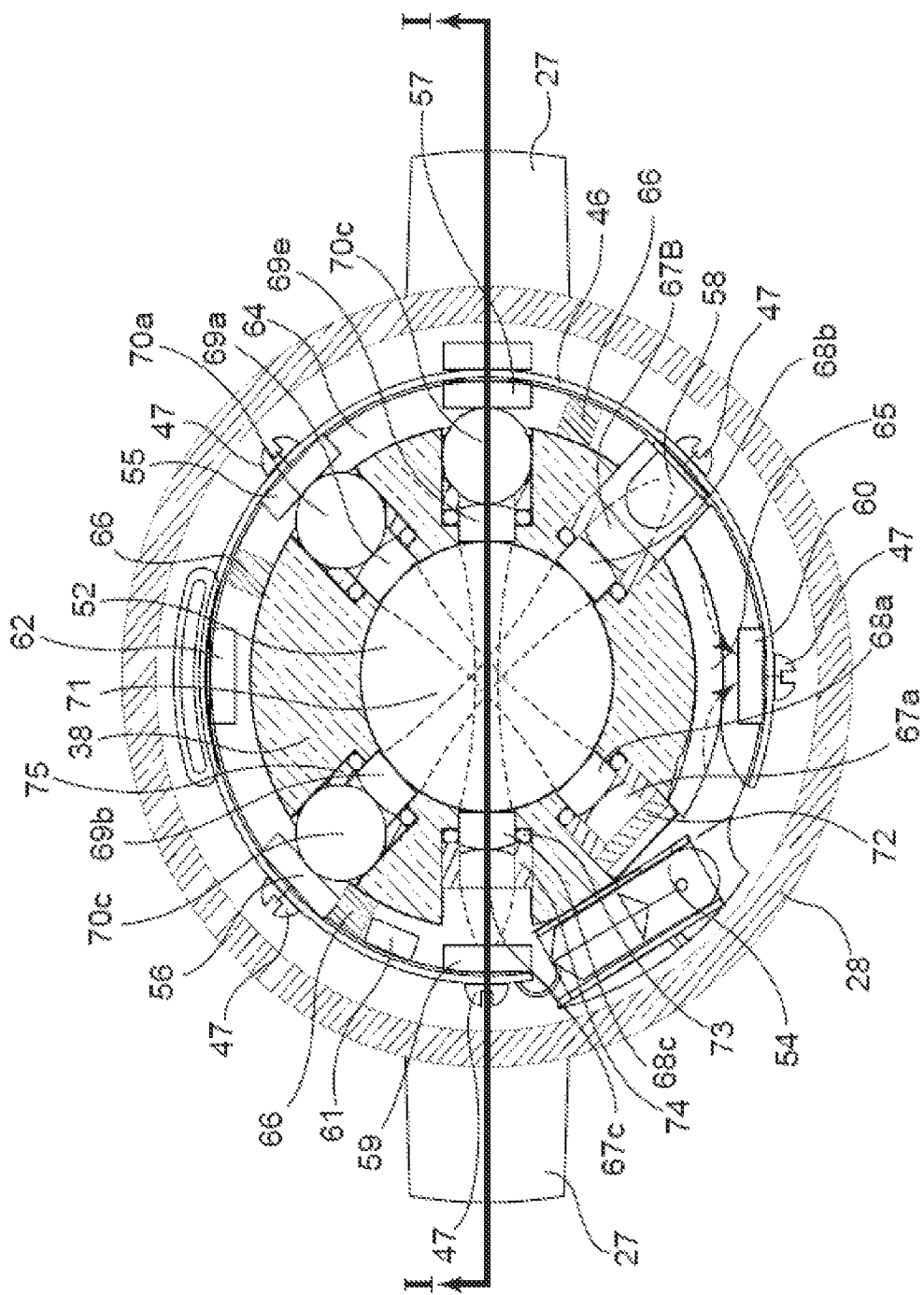
FIG. 7 shows a cross-sectional view of an example sensor head of the multi-channel device taken through the centers of optical channels.

The optical channels are arranged symmetrically to an axis of sample compartment 52 and passing the axis of sample compartment 52 as shown in more detail with respect to FIG. 7.

Figure 6:
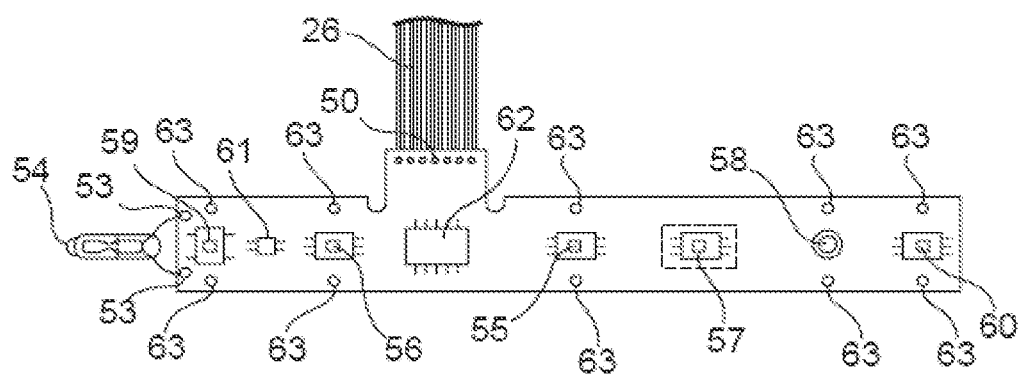
FIG. 6 shows a view of an example sensor flex board with an EPA lamp, an RGB LED, UV LED, RGB detector, two main detectors and two reference detectors.

FIG. 6 shows the inside surface of flex board 46 on which opto-electronic components are placed. Flex board 46 has contact holes 53 for soldering a first light source 54 for the turbidity channel. First light source 54 may be a tungsten lamp, an infrared LED or other appropriate light source. A first main detector 55 (direct turbidity channel) and a second main detector 56 (color channel and scattered turbidity channel) are photodiodes with frequency outputs. A third main detector 57 (direct colorimetric channel) is a RGB detector with frequency output. A second light source 58 is for the color channel. Second light source 58 may be, for example, an ultraviolet LED. A third light source 59 is for the colorimetric channel. Third light source 59 may be, for example, a tri-color RGB (Red-Green-Blue) LED 59. A first reference detector 60 is a photodiode with frequency output. After flex board 46 is wrapped around sample holder body 38, a first reference detector 60 is positioned between tungsten lamp 54 and ultraviolet LED 58. First reference detector 60 monitors the intensity of both light sources 54 and 58. A second reference detector 61 monitors the intensity of red, green and blue LEDs of the tri-color RGB LED 59. Second reference detector may be, for example, a photodiode with I$^2$C communication.

An electronic chip 62 is a second I/O expander. Two input/output expanders are used to allow the same I$^2$C communication line to be used for receiving signals from temperature sensor 49 and from second reference detector 61, for setting sensitivity of main detectors 55, 56, 57 and for setting intensity of the five light sources: tungsten lamp 54, ultraviolet LED 58 and red, green and blue LEDs of the tri-color RGB LED 59. Mounting holes 63 allow flex board 46 to be secured to sample holder body 38 using screws 47 as shown in FIG. 5.

FIG. 7 shows a cross-sectional view of sensor head 3 of the multi-channel device 100 taken through the centers of the optical channels, which are located in the same horizontal plane. The three optical channels, indicated by dashed lines extending through sample compartment 52 in the center of sample holder body 38, are variable diameter cylindrical bores through sample holder body 38. Screws 47 secure flex board 46 to sample holder body 38. A groove 64 under the central part of flex board 46 accommodates the light sources and the detectors. Between tungsten lamp 54 and ultraviolet LED 58 groove 64 has a deeper portion 65, which forms a scattering cavity allowing first reference detector 60 to receive signals from both light sources 54 and 58. Light absorbing members 66 in groove 64 protect first main detector 55 and second main detector 56 from scattered light traveling in groove 64. Opaque cover 28 protects detectors 55, 56 and 57 from ambient light.

Each optical channel has an excitation (i.e., light source side) sub-channel with focusing optics (positive lenses 67*a* and 68*a*, 67*b* and 68*b*, 67*c* and 68*c*) to form an excitation beam. Each optical channel also has an emission (i.e., detector side) sub-channel with focusing optics (positive lenses 69*a*, 69*b*, 69*c* and ball lenses 70*a*, 70*b*, 70*c*) to gather direct or scattered radiation on the corresponding detector.

For the turbidity channel, tungsten lamp 54 emits an excitation beam, part of which travels through focusing optics (positive lenses 67*a* and 68*a*) and is directed through the sample compartment 52 into a sample solution 71. After passing through sample solution 71 the transmitted direct light travels to positive lens 69*a* and ball lens 70*a*, which gather the transmitted light at the first main detector 55. The excitation beam from tungsten lamp 54 passing through sample solution 71 also produces a scattered light. Part of the scattered light travels to focusing optics (positive lens 69*b* and ball lens 70*b*), which direct it to second main detector 56. Another part of the excitation beam from tungsten lamp 54 travels through groove 64 and deeper portion 65 and reaches first reference detector 60, which produces a reference signal proportional to the instantaneous intensity of tungsten lamp 54. A green filter 72 is provided between tungsten lamp 54 and first focusing optics to correct the spectral distribution of the detector according to EPA specifications.

For the color channel, ultraviolet LED 58 emits UV radiation, part of which travels through focusing optics (positive lenses 67*b* and 68*b*) and is directed through the sample compartment 52 into sample solution 71. After passing through sample solution 71, the transmitted direct light travels to positive lens 69*b* and ball lens 70*b*, which gather the transmitted light at second main detector 56. Part of the UV radiation from ultraviolet LED 58 travels through groove 64 and deeper portion 65 and reaches first reference detector 60, which produces a reference signal proportional to the instantaneous intensity of ultraviolet LED 58.

For the colorimetric channel, tri-color RGB LED 59 emits red, green or blue light, part of which travels through focusing optics (positive lenses 67*c* and 68*c*) and is directed through sample compartment 52 into sample solution 71. After passing through sample solution 71 the transmitted direct light travels to positive lens 69*c* and ball lens 70*c*, which gather the transmitted light at third main detector 57. The spectral emission of the tri-color RGB LED 59 and the spectral sensitivity of third main detector 57 should be set according to a specific colorimetric procedure, which is chosen for the current measurement. Part of light from tri-color RGB LED 59 travels through groove 64 and reaches second reference detector 61, which produces a reference signal proportional to the instantaneous intensity of the spectral emission of tri-color RGB LED 59.

The six positive lenses 68A, 68B, 68C, 69A, 69B, 69C are placed in the variable diameter cylindrical lens channels with their axis perpendicular to the axis of the sample compartment 52. They work as windows for the sample compartment 52. Each cylindrical lens channel has smaller diameters in an internal part (that is, toward the center of sample compartment 52) and increased diameter in external part (that is, toward the perimeter of sample compartment 52) as indicated by the dashed lines in FIG. 7. The smaller diameters of lens channels and outside diameters of positive lenses 68A, 68B, 68C, 69A, 69B, 69C to provide a press-fit tolerance in the internal part of channel, which is close to the sample compartment 52. Six o-rings 73 are compressed around positive lenses 68A, 68B, 68C, 69A, 69B, 69C. External positive lenses 67A, 67B, 67C are first assembled in a press-fit manner inside of lens inserts 74 and then lens inserts 74 with lenses are set in a press-fit manner in external parts of lens channels providing additional compression to the o-rings in those channels. Three ball inserts 75 are set in a press fit manner in external part of the lens channels. Then ball lenses 70A, 70B, 70C are set in a press fit manner to provide additional compression to the o-rings in those channels. This described assembling procedure allows sealing the sample compartment having six optical channels with micro-optics using minimal number of parts. However, it shall be understood that the multi-channel device 100 need not be assembled in this manner, and that the invention is not limited in this respect.

Figure 8:
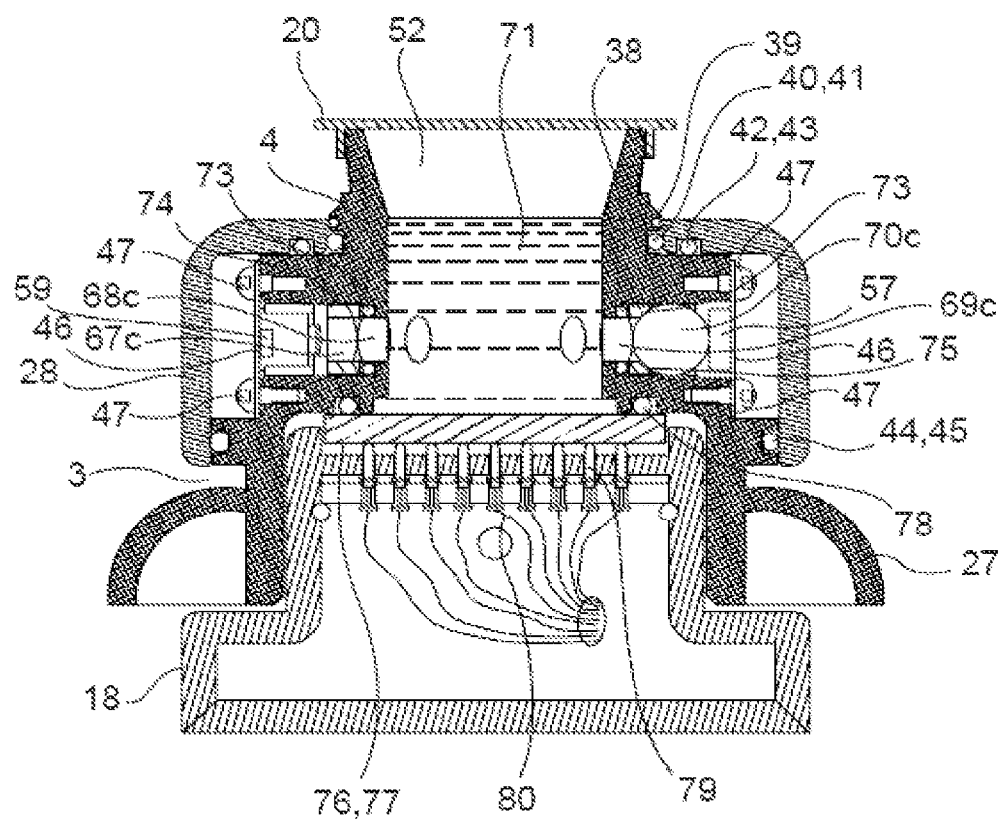
FIG. 8 shows a vertical cross-section (I-I section) of the example sensor head of FIG. 7.

FIG. 8 shows a vertical cross-section taken along lines I-I in FIG. 7 of the sensor head 3 through the centers of wings 27. The sensor head 3 is positioned on bayonet mount 18. Sensor head 3 includes sample holder 4 having wings 27, sample compartment 52 and sample holder body 38. Sample holder body 38 includes a snap rib 39, a groove 40 for o-ring 41, a groove 44 for o-ring 45, threaded holes for mounting screws 47, which secure flex board 46, groove 64 for opto-electronic components and cylindrical channels with variable diameters for focusing optics. Opaque cover28 protects the opto-electronics from ambient light.

FIG. 8 shows the opto-electronic components for the colorimetric channel. Tri-color RGB LED 59 is soldered to flex board 46 and produces red, green or blue light according to the specific colorimetric calibration being performed, which is chosen for the analyte concentration to be determined. The excitation focusing optics, positive lenses 67C and 68, produce an excitation beam traveling through the sample compartment 52 filled with sample solution 71. Part of the light from the tri-color RGB LED 59 travels to second reference detector 61 (not shown in FIG. 8). To make an analysis for a specific analyte a sample of water is mixed with a specific chemical compound(s) to produce a colorimetric reaction in the sample solution. The colorimetric reaction is a change in absorbance of the sample solution that is proportional to the analyte concentration. The emission focusing optics, positive lens 69c and ball lens 70, direct the transmitted light to third main detector 57. Signals from the reference detector 61 and the third main detector 57 are processed by the sensor controller board 9 to evaluate the concentration of analyte in a water sample.

In one example embodiment, a separable bottom disk 76 hermetically seals the bottom part of sample compartment 52 when sensor head 3 is locked on bayonet mount 18. Separable disk 76 allows for cleaning of the optical parts inside sample holder 4. In another example embodiment, separable disk 76 may include a replaceable non-optical sensor unit 77, which is directly placed underneath sample compartment 52, with only o-ring 78 in-between. Replaceable non-optical sensor unit 77 is also shaped as a disk and includes at least one of a temperature sensor, a conductivity sensor, a pH sensor, an electrochemical sensor and the like. Signals generated by non-optical sensor unit 77 are transmitted via spring contacts 79 connected with connection wires 80, which are then connected with the reader controller board 12, which processes data to evaluated non-optical parameters.

Figure 9:
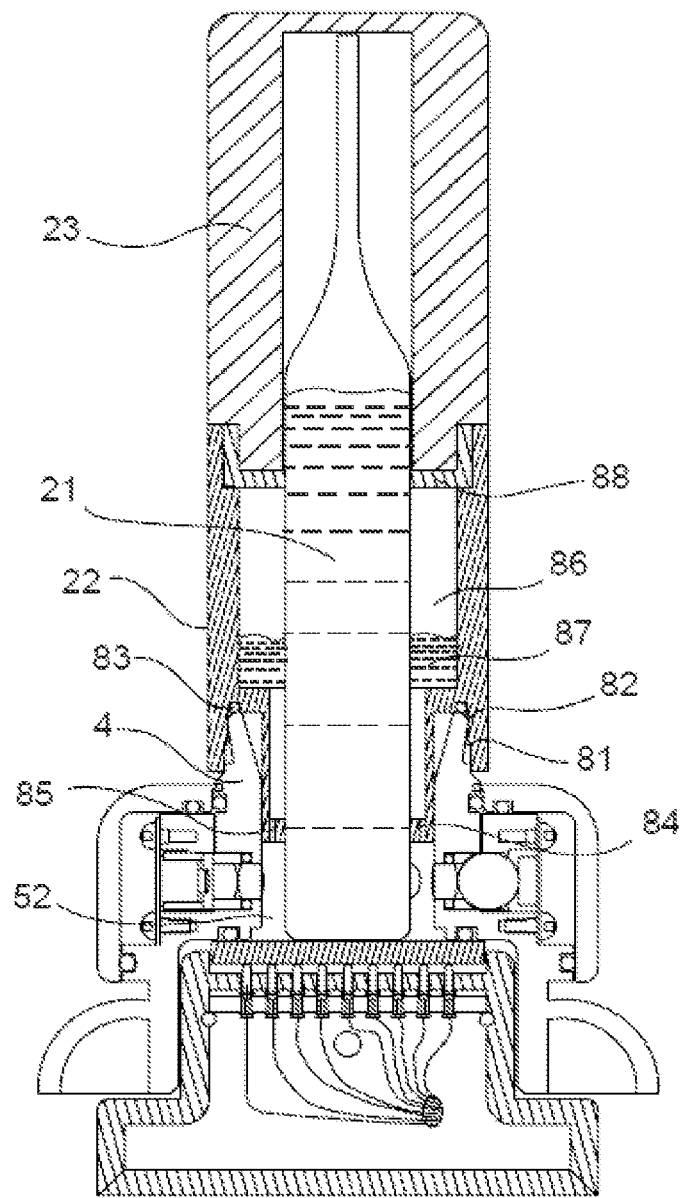
FIG. 9 shows a vertical cross-section of an example sensor head through the centers of wings 27 in the mode when sensor unit 1 is calibrated for using a colorimetric test ampoule 21.

FIG. 9 shows a vertical cross-section of sensor head 3 through the centers of wings 27 in a mode when sensor unit 1 is calibrated for using a colorimetric test ampoule 21 to measure specific analytes in water samples. In this mode sample compartment 52 is filled with clean water (distilled, for example). The volume of water for the embodiment shown in FIG. 9 may range from 3 ml to 5 ml. An ampoule holder 22 is set on the top opening of sample holder 4. Ampoule holder 22 is made of opaque material and may include a positioning ring 81 with an internal groove 82 to provide a locking action when ampoule holder 22 is snapped onto sample holder 4. An o-ring 83 protects from spilling water over the neck of sample holder 4 when test ampoule 21 is placed in ampoule holder 22. A centering piece 84 is located at the lower part of ampoule holder 22. Centering piece 84 may be made as several flexible members 85 to accommodate test ampoules of various diameters and to facilitate the placement of these differently sized ampoules firmly in the center of sample compartment 52. Flexible members 85 end above the optical channels and may include slits or openings to allow movement of water when a test ampoule is inserted. The central part of ampoule holder 22 includes a cavity 86, which is a reservoir for water 87 forced out of sample compartment 52 during test ampoule insertion. A disk 88 at the top of ampoule holder prevents ampoule tilting during measurement. Ampoule cover 23 is made of opaque material for protection from ambient light.

Figure 10:
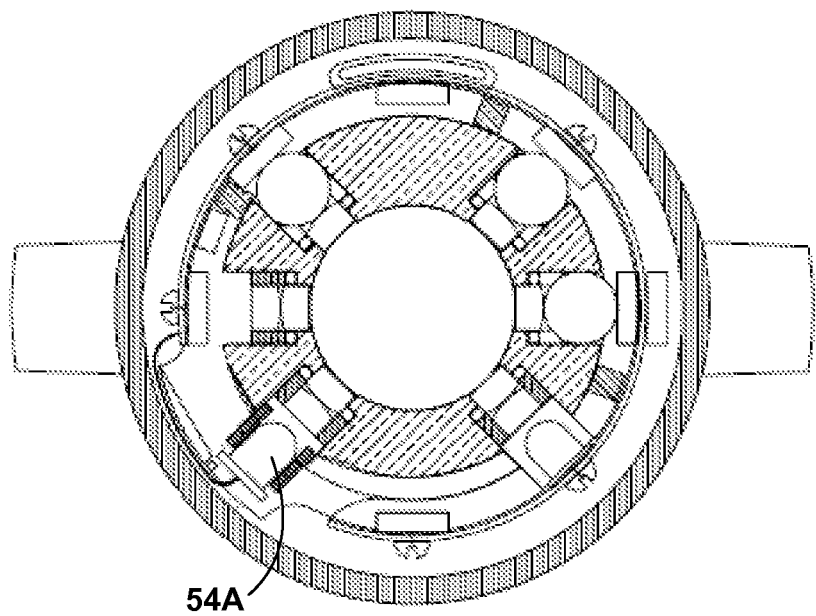
FIG. 10 shows another vertical cross-section of an example sensor head.

FIG. 10 shows a cross-sectional view of another example sensor head. FIG. 10 differs from FIG. 7 in that there filter 72 is removed and lamp 54 is replaced by IR LED 54A.

Figure 11:
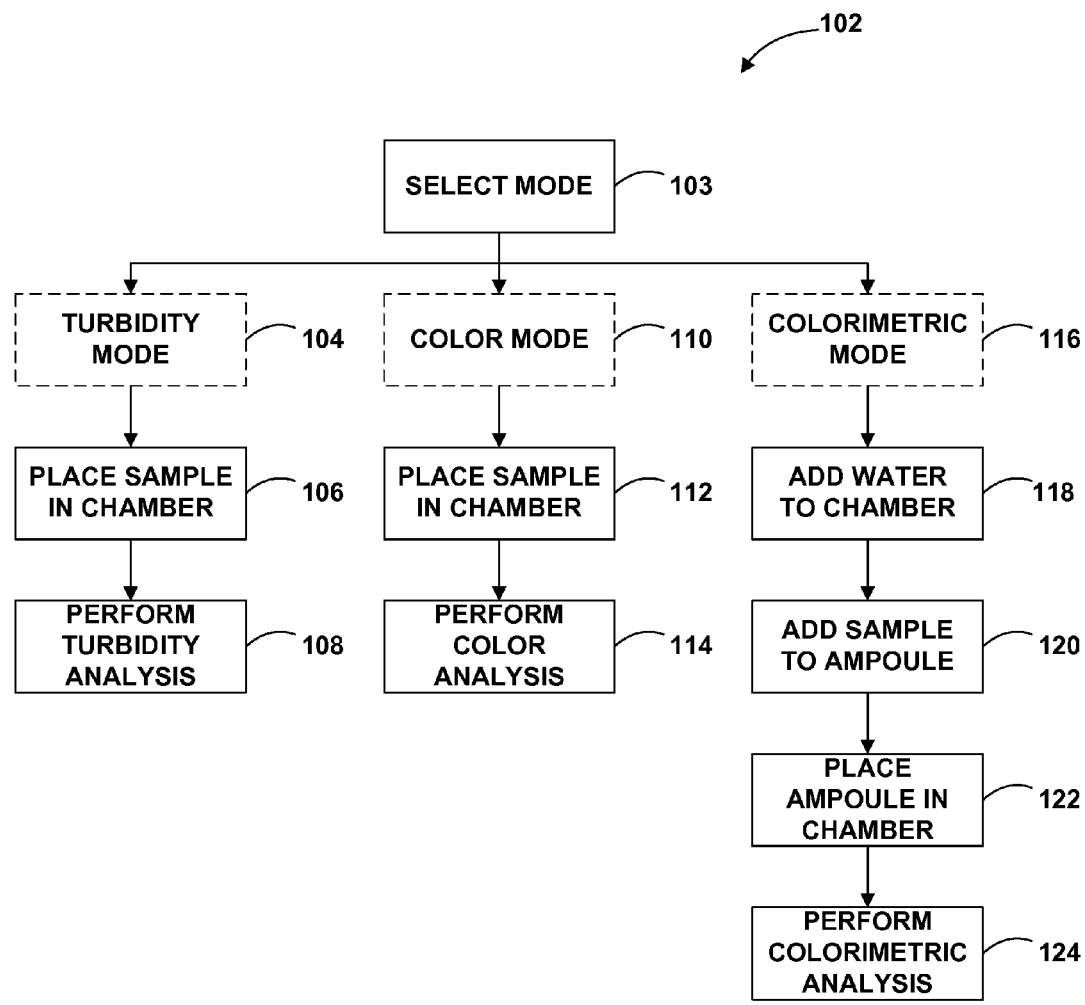
FIG. 11 is a flow chart illustrating an example process by which multi-channel device measures various properties of a water sample.

FIG. 11 is a flow chart illustrating an example process (102) of using multi-channel device 100 to measure various properties of a water sample. For example, FIG. 11 illustrates an example process of using multi-channel device 100 to measure turbidity of a water sample, color of a water sample or concentration of an analyte in a water sample.

As shown in FIG. 11, a user selects the desired mode for multi-channel device 100 corresponding to the desired measurement to be made (103). In the example embodiment of multi-channel device shown in FIG. 11, there are three main modes: a turbidity mode (104), a color mode (110) and a colorimetric mode (116). In turbidity mode (104) the sample to be analyzed is placed in sample chamber 52 of the multi-channel device 100 (see, e.g., FIGS. 4, 5, 7 and 8). Processor 30 on sensor controller board 9 performs the turbidity analysis (108). The turbidity analysis performed in turbidity mode is described in further detail herein below and with respect to FIG. 12. In color mode (110) the sample to be analyzed is placed in sample chamber 52 of the multi-channel device 100. Processor 30 performs the color analysis (114). The color analysis performed in color mode is described in further detail herein below and with respect to FIGS. 13 and 14.

In colorimetric mode (116), before a measurement takes place, water is added to the sample chamber 52 (see, e.g., FIG. 9). A test ampoule 21 containing an appropriate reagent chemical is chosen based upon the analyte in the sample to be measured. The sample is then added to ampoule (120). After the ampoule 21, has been prepared, it is placed in the water-containing sample chamber 52 (122). Depending upon the amount of water that was added to the sample chamber, some of the water may overflow into reservoir 86 after the ampoule is inserted into sample chamber 52. Once ampoule 21 is positioned within sample chamber 52, processor 30 performs the colorimetric analysis (124).

Addition of water to the sample chamber 52 in colorimetric mode increases the accuracy of the colorimetric measurements made by multi-channel device 100. This is because water in the chamber and the glass ampoule have similar refractive indices. Light reflectance at the water/ampoule boundary is therefore reduced in comparison with an ampoule placed in air. In addition, when the ampoule is placed in water the optical system may become less sensitive to variations in positioning of the ampoule in sample chamber 52 because presence of water compensates for the focusing action of the cylindrical ampoule body.

In some embodiments, multi-channel device 100 may include more than one colorimetric mode 116. For example, multi-channel device 100 may include any or all of the following colorimetric modes: a red-red colorimetric mode (red light source, red detector), a green-green colorimetric mode (green light source, green detector), a blue-blue colorimetric mode (blue light source, blue detector), a green-red colorimetric mode (green light source, red detector) and/or a so-called fluoride mode (green light source, red detector) that measures a discoloration of chemical component in presence of fluoride. Each of these colorimetric modes are described in detail below with respect to FIGS. 15-22. In some other embodiments, multi-channel device 100 may also include a red-green colorimetric mode (red light source, green detector), a green-blue colorimetric mode (green light source, blue detector), a blue-green colorimetric mode (blue light source, green detector) or a UV-UV colorimetric mode (UV light source, UV detector).

The turbidity mode, color mode and colorimetric modes will now be described in further detail. In the following discussion of these modes, each set of coefficients are specific for each light source-detector combination ($c_1$, $c_2$, $c_3$, $c_4$) and for each analyte ($c_5$).

Turbidity Mode

When in turbidity mode (104) processor 30 performs a turbidity analysis to measure the turbidity of the sample placed in sample chamber 52. Once turbidity mode is selected (104), a set of constants are loaded from memory 31 as follows:

light source setting (e.g., tungsten lamp 54 in FIG. 7 or an IR LED (such as is shown in FIG. 10); also identifies the appropriate detector, in this case first main detector 55)

equation type (equation for $c_1$ during turbidity calculations)

Dz, Sz, Rz—direct, scattered, reference signal during zeroing,

Lambda, K—turbidity correction coefficients, K=0 in turbidity mode

N—normalization (scale) coefficient,

A(Range0), B(Range0), C(Range0), D(Range0), E(Range0), K3(Range0), K4(Range0)—linearization coefficients for range 0, A(Range1), B(Range1), C(Range1), D(Range1), E(Range1), K3(Range1), K4(Range1)—linearization coefficients for range 1, A(Range2), B(Range2), C(Range2), D(Range2), E(Range2), K3(Range2), K4(Range2),—linearization coefficients for range 2, Thresh0, Thresh1—thresholds of transition between ranges, Alpha—user calibration coefficient, K1, K2, and tc—temperature correction coefficients.

Next a measurement is taken, resulting in the raw values Dm (direct signal as measured by first main detector 55), Sm (scattered signal as measured by second main detector 56) and Rm (light source signal as measured by reference detector 60) are recorded. Dm, Sm and Rm are direct, scattered, reference signal during measurement.

The optical signal from the measured values Dm, Sm and Rm and is corrected for instability of the turbidity mode light source using the Dz, Sz and Rz constants that were measured and stored before analysis of the unknown sample. For example, raw optical signal corrected for instability of the turbidity mode light source, $c_1$, may be expressed as follows:

$$c_1 = ((Sm/Rm) - (Sz/Rz)) * ((Dz/Dm)/Rz * Rm).$$

Figure 12:
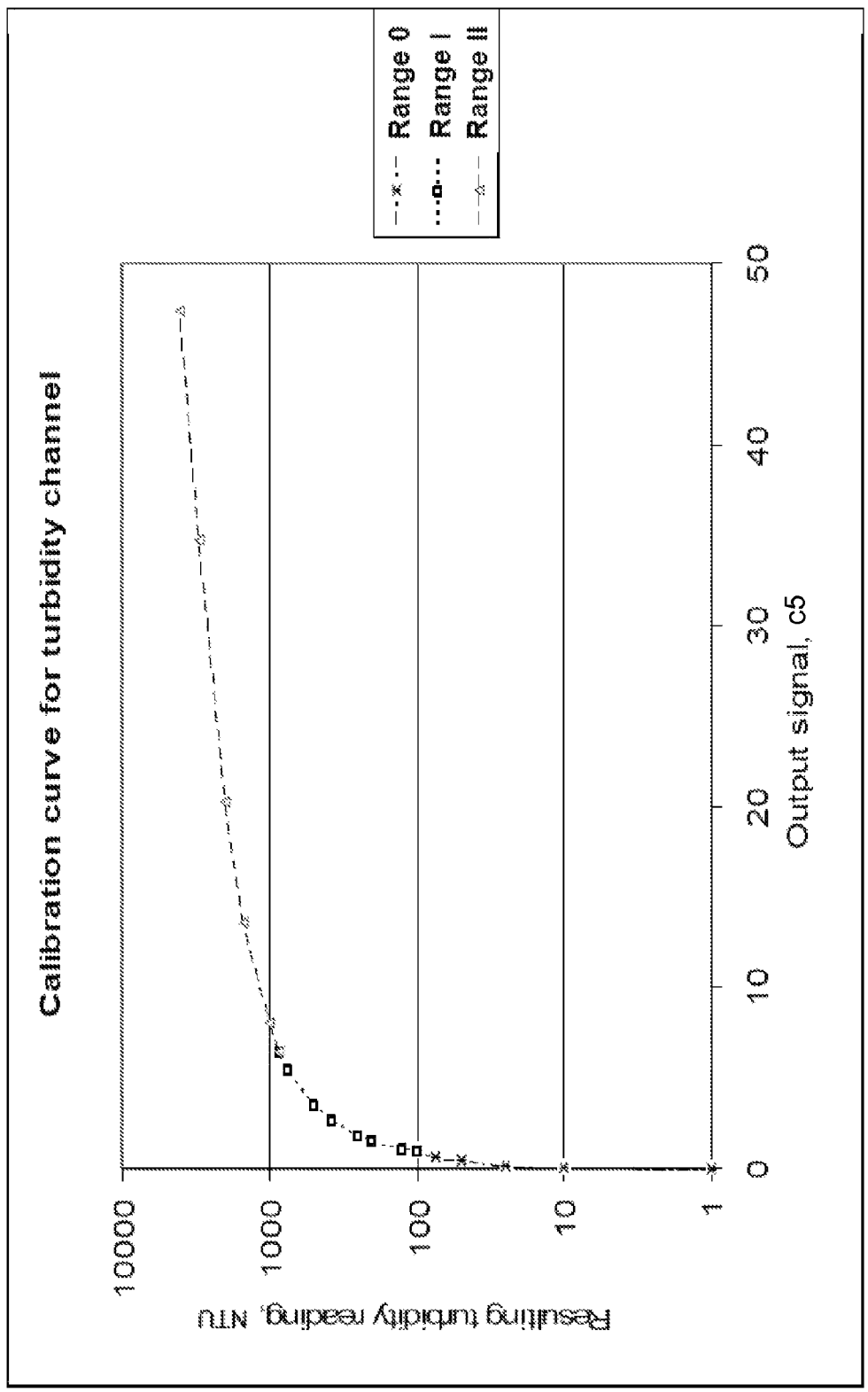
FIG. 12 is a graph illustrating example linearization and normalization during processing for the turbidity channel.

The raw optical signal $c_1$ is then normalized. FIG. 12 is a graph that illustrates, among other things, an optical signal curve, $c_2$, versus turbidity over a turbidity range of 0 to 4000 NTU. The purpose of normalization is to ensure consistent readings for all manufactured multi-channel devices. Thus, at the time of manufacture or at some other time prior to analysis of an unknown sample, each individual multi-channel device 100 measures a sample of known turbidity (e.g., 100 NTU). Each multi-channel device 100 then calculates and stores a normalization coefficient, N, which scales its measurement to correspond to the known turbidity value. For example, each unit may calculate and store a normalization coefficient N such that it's resulting measurement is scaled to 100 NTU for a sample of known turbidity 100 NTU. The normalized optical signal, $c_2$, may be expressed as follows:

$$c_2 = c_1 * N.$$

Following normalization, a linearization process is performed. To simplify calculation and increase processing speed, curve $c_2$ may be divided into three ranges, indicated in FIG. 12 by Range0, Range1 and RangeII. In each range, the optical signal curve $c_2$ may be approximated by a linear relationship. Two thresholds, Thresh0 and Thresh1, define the boundaries between the ranges. The equations approximating the optical signal curve $c_2$ in each range, $c_5$, are as follows:

When $c_2 <$ Thresh0 (Range 0), the optical signal curve $c_2$ is nearly linear. Therefore, in Range 0, the optical signal curve $c_2$ may be approximated by the equation:

$$c_5 = (A(Range0) * (E(Range0) + c_2 * (1.0 + c_2 * (B(Range0) + c_2 * (C(Range0) + c_2 * D(Range0)))) + K3(Range0) * (c_2 \wedge (2 * K4(Range0)))))$$

When Thresh0 $< c_2 <$ Thresh1 (Range I), the optical signal curve $c_2$ is not accurately represented by a linear relationship. Therefore, in Range I (and likewise in Range II), the optical signal curve $c_2$ is adjusted by taking the square root as follows:

$$c_4 = \sqrt{c_2}.$$

The adjusted optical signal curve, $c_5$, is illustrated in FIG. 12. The adjusted optical signal curve $c_5$ in Range I may be approximated by the equation:

$$c_5 = (A(Range1) * (E(Range1) + c_4 * (1.0 + c_4 * (B(Range1) + c_4 * (C(Range1) + c_4 * D(Range1)))) + K3(Range1) * (c_4 \wedge (2 * K4(Range1)))))$$

When $c2 > Thresh1$ (Range II), again $c4 = \sqrt{c2}$, and the adjusted optical signal curve c5 in Range II may be approximated by the equation:

$$c5 = (A(Range2) * (E(Range2) + c4 * (1.0 +$$
$$c4 * (B(Range2) + c4 * (C(Range2) + c4 * D(Range2)))) +$$
$$K3(Range2) * (c4 \wedge (2 * K4(Range2))))).$$

FIG. 12 also illustrates the approximated optical signal curves c5 in each range.

To continue the turbidity analysis, an end user calibration is applied such that $$c6 = Alpha * c5,$$

where Alpha is an end user calibration coefficient. During factory calibration the Alpha coefficient is set to default value 1. The coefficient Alpha can be periodically adjusted to compensate for aging of the light sources and the detectors. Alpha is determined by measuring of turbidity standards with a known turbidity value (TurbStand) and comparing it to an actual reading (TurbRead). The corrected new value of Alpha may be calculated using an equation AlphaNew=AlphaOld*TurbStand/TurbRead.

Variations in temperature may have an effect on the resulting turbidity reading. A temperature correction may therefore be applied as follows:

$$c7 = c6 * (1 + K1 * (tm - tc) + K2 * ((tm - tc)^2)),$$

where tm is the current temperature during analysis of the sample, tc is the temperature at which the unit was calibrated and K1 and K2 are temperature correction coefficients. K1 and K2 are determined after temperature tests during sensor fabrication and stored in sensor's memory 31.

The value c7 is the resulting turbidity reading. This reading may be displayed on display 13 of multi-channel device 100 and/or may be sent to an external device via RS-232 or USB connection 11 (see FIG. 1).

Color Mode

Referring again to FIG. 11, when in color mode (110) processor 30 performs a color analysis to measure the color of the sample placed in sample chamber 52. Once color mode is selected (110), a set of constants are loaded from memory 31 as follows (although the same constant names are used for turbidity, color and colorimetric modes, it is to be understood that the values are different for each mode):

light source setting (e.g., UV LED 58 in FIG. 7; also specifies second main detector 56);

equation type (equation for c1 during color calculations);

Dz, Rz—direct signal measured by second main detector and reference signal measured by reference detector during zeroing, respectively;

R, S, U, V—preliminary linearization coefficients;

Lambda, K—color correction coefficients;

N—normalization (scale) coefficient;

A(Range0), B(Range0), C(Range0), D(Range0), E(Range0), K3(Range0), K4(Range0)—linearization coefficients for range 0;

A(Range1), B(Range1), C(Range1), D(Range1), E(Range1), K3(Range1), K4(Range1)—linearization coefficients for range 1;

A(Range2), B(Range2), C(Range2), D(Range2), E(Range2), K3(Range2), K4(Range2)—linearization coefficients for range 2;

Thresh0, Thresh1—thresholds of transition between ranges;

Alpha—user calibration coefficient;

K1, K2, and tc—temperature correction coefficients.

The optical density calculated from the measured values Dm and Rm is corrected for instability of the color mode light source using the Dz and Rz constants that were measured and stored before analysis of the unknown sample. For example, raw optical density corrected for instability of the color mode light source between zero and the time of measurement, c1, may be expressed as follows:

$$c1 = \log 10((Dz * Rm)/(Dm * Rz)).$$

Figure 13:
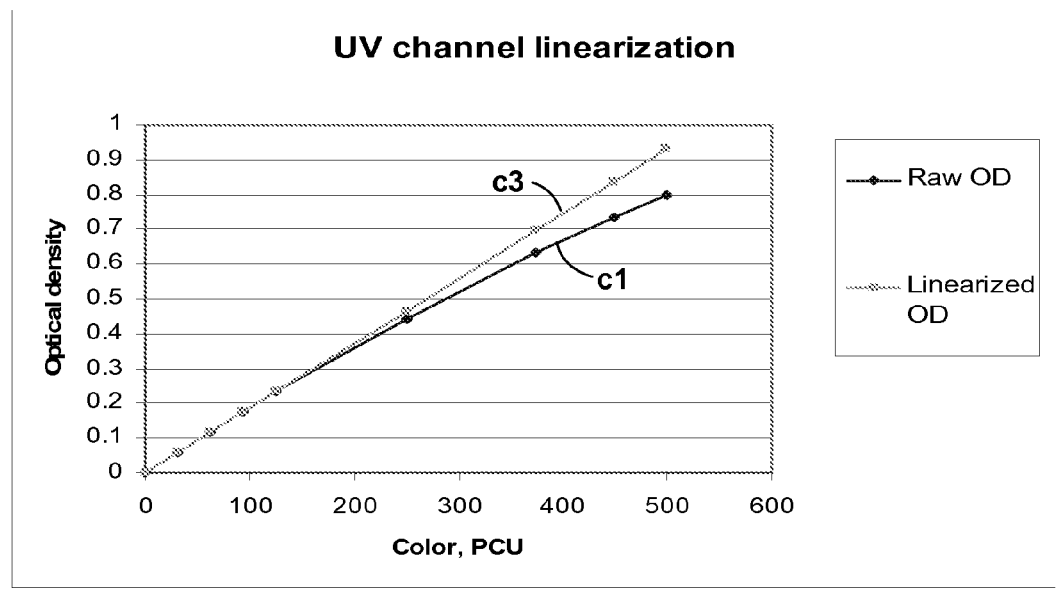
FIGS. 13-14 are graphs illustrating example linearization and normalization during processing for the color channel.

An example corrected raw optical density curve, c1, is shown in FIG. 13. A first linearization function is then applied to the raw optical density, c1, to arrive at a linearized optical density, c3, as follows:

$$c3 = (c1 * (R + c1 * (S + c1 * (V + U * c1)))),$$

where R, S, V and U are preliminary linearization coefficients. These preliminary linearization coefficients are determined by measuring several color standards in ampoules and calculating coefficients to have minimal deviations from linearity. An example linearized optical density curve c3 is also shown in FIG. 13.

Next, a normalization function is applied to arrive at a normalized optical density, c4, as follows:

$$c4 = c3 * (1 + Lambda).$$

Figure 14:
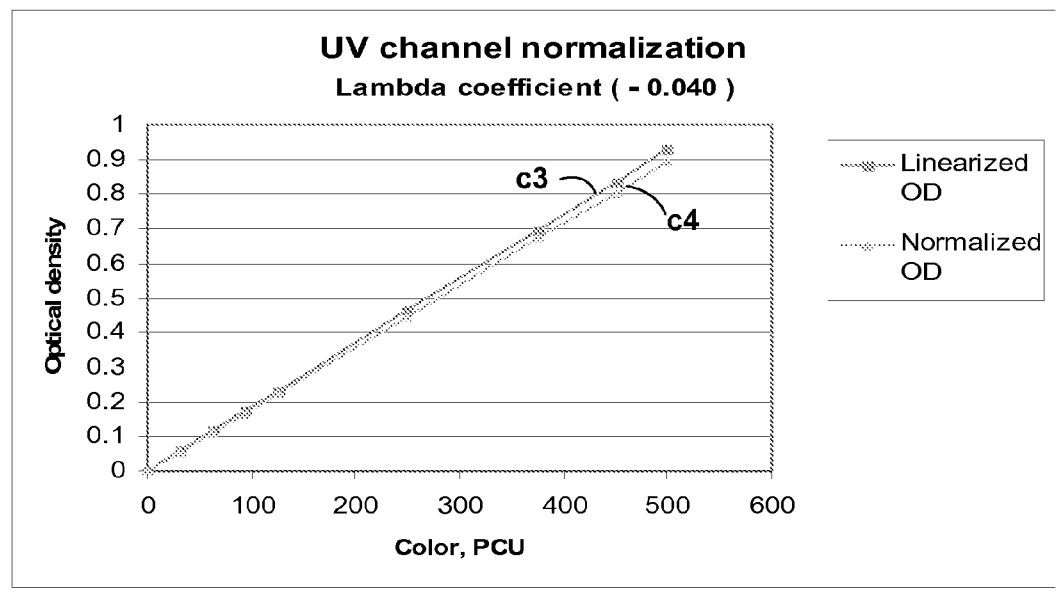

The color correction coefficient Lambda is unique to each multi-channel device 100, and is chosen such that each device 100 reads a predefined optical density at a predefined unit of color. For example, a color correction coefficient Lambda may be calculated for each multi-channel device 100 such that each device 100 reads an optical density of 0.8 at 450 PCU (platinum-cobalt units, a standard measure of color). An example linearized optical density, c3, and an example normalized optical density, c4, is illustrated in FIG. 14.

Finally a color calibration curve c5 for measuring of color when water sample is placed in chamber may be approximated using the following equation:

$$c5 = (A(Range0) * (E(Range0) + c4 * (1.0 +$$
$$c4 * (B(Range0) + c4 * (C(Range0) + c4 * D(Range0)))) +$$
$$K3(Range0) * (c4 \wedge (2 * K4(Range0))))).$$

Because normalized optical density curve c4 is very nearly linear, the entire curve c5 may be approximated with a single equation. Thus, the value of Thresh0 is set so that only one range (range 0) is used in the calculation. Next the end user calibration is applied such that $$c6 = Alpha * c5.$$

The temperature correction may also be applied resulting in $$c7 = c6 * (1 + K1 * (tm - tc) + K2 * ((tm - tc)^2)).$$

The value c7 is the resulting color reading. This reading may be displayed on display 13 of multi-channel device 100 and/or may be sent to an external device via RS-232 or USB connection 11 (see FIG. 1).

When color channel (UV light source and UV detector) is used as colorimetric channel (see explanation for colorimetric modes below) the normalization step for c4 includes an additional variable coefficient K $$c4=c3*(1+(K*\text{Lambda})).$$

The analyte specific coefficient K compensates for variations in optical properties of color standards which is used for calibration of individual units and colored chemical compound which is used for measuring of said analytes.

Next calculation for colorimetric variant of color (UV) channel are the same as described above c5, c6, c7 with appropriate for each analyte coefficients for final calibration and temperature correction.

Colorimetric Mode(s)

Referring again to FIG. 11, multi-channel device 100 includes at least one colorimetric mode (116). When in a colorimetric mode, multi-channel device 100 determines the concentration of an analyte in the sample solution by measuring the intensity of the color (e.g., optical density) produced by a colorimetric reaction between a reagent chemical compound and the sample. Multi-channel device 100 then relates the intensity of the color produced to the concentration of the analyte in the sample.

In colorimetric mode (116), before a measurement takes place, water is added to the sample chamber 52 (see, e.g., FIG. 9). A test ampoule 21 containing an appropriate reagent chemical is chosen based upon the analyte in the sample to be measured. Sample is then added to the ampoule 21 (120). For example, test ampoule 21 may be inverted and cracked in a volume of the sample. Atmospheric pressure then pushes the liquid sample inside of test ampoule 21, thus mixing the liquid sample and the chemical compound to produce a colorimetric reaction inside of test ampoule 21.

After test ampoule 21 has been prepared, it is placed in the water-containing sample chamber 52 (122). Depending upon the amount of water that was added to the sample chamber, some of the water may overflow into reservoir 86 after the ampoule is inserted into sample chamber 52. Once ampoule 21 is positioned within sample chamber 52, processor 30 performs the colorimetric analysis (124).

Multi-channel device 100 includes at least one colorimetric mode (116). For example, multi-channel device 100 may include any or all of the following colorimetric modes: a red-red colorimetric mode (red light source, red detector), a green-green colorimetric mode (green light source, green detector), a blue-blue colorimetric mode (blue light source, blue detector), a green-red colorimetric mode (green light source, red detector) and/or a so-called fluoride mode (green light source, red detector). Some of these colorimetric modes will now be described.

In the colorimetric modes and the fluoride mode, several coefficients may be used to calibrate each individual multi-channel device, which may improve the accuracy of the resulting measured analyte concentration. For example, a Lambda coefficient, specific to each multi-channel device, may be determined, where Lambda is a function of each unit such that each unit measures a chosen optical density for a chosen concentration of a dye standard. If the particular multi-channel device being calibrated returns the chosen optical density, then the Lambda coefficient for that unit would be 0. The Lambda coefficient is adjusted for each unit accordingly.

A correction coefficient K specific to each analyte may also be determined, where K is a function of the optical properties of the analyte as compared to the optical properties of a dye standard.

The dye standard may be chosen such that the optical density is fairly linear over an optical density range of interest, such as between 0-2. The optical density curve of the dye standard need not be exactly linear or even substantially linear—linearity within ±30% is acceptable.

An example process of calibrating the multi-channel device 100 is as follows. A dye standard is selected for calibrating a colorimetric channel in a multi-channel device that measures concentration of an analyte in a liquid sample. A plurality of dye standard samples are then prepared having concentrations corresponding to an optical density range of interest. Each dye standard sample is placed in chamber 52, and the optical density data for each of the plurality of dye standard samples is collected. A linearization procedure is applied to the optical density data to generate a linearized optical density curve for those instances in which the optical density curve is non-linear. A normalization coefficient is applied to the linearized optical density curve to generate a generic normalized optical density curve. The normalization ensures a chosen concentration of the dye standard corresponds to a chosen optical density.

A plurality of analyte standard samples having concentrations corresponding to a effective analytical range of colorimetric are prepared. Raw optical density data is collected for each of the plurality of analyte standard samples. A linearization procedure and the normalization coefficient are applied to the raw optical density data to determine a normalized optical density for each of analyte standard samples. A generic calibration curve is then determined using concentration of the analyte standards and normalized optical density.

When determining the analyte concentration of an unknown sample, the sample optical density data for the sample is obtained, and a preliminary analyte concentration determined from the normalized optical density curve. The Lambda coefficient may then be applied to compensate for any variation that may be attributed to the particular unit doing the measurement. The correction coefficient K may also be applied to compensate for variations due to differences in optical properties of the analyte as compared to optical properties of the dye. A temperature correction coefficient may also be applied to compensate for differences in the measured analyte concentration due to temperature variations.

More details concerning the processing during the colorimetric and fluoride modes are given below.

Red-Red Colorimetric Mode

When measuring a photometric analyte using a red light source and a red detector, the red-red colorimetric mode is selected and a set of constants are loaded from memory 31 as follows (although the same constant names are used for turbidity, color and for each of the colorimetric modes, it is to be understood that the values are different for each mode):

lightsource, equation, Dz, Sz, Rz, RB, R, S, U, V, Lambda, K, N, A(Range0), B(Range0), C(Range0), D(Range0), E(Range0), K3(Range0), K4(Range0), A(Range1), B(Range1), C(Range1), D(Range1), E(Range1), K3(Range1), K4(Range1), A(Range2), B(Range2), C(Range2), D(Range2), E(Range2), K3(Range2), K4(Range2), K1, K2, Alpha, Thresh0, Thresh1 and tc calibration coefficients. The direct (Dm) and reference (Rm) signal measurements are obtained and recorded.

The optical density calculated from the measured values Dm and Rm is corrected for instability of the colorimetric mode light source (e.g., tri-color LED 59) using the Dz and Rz constants that were measured and stored before analysis of the unknown sample. For example, raw optical density corrected for instability of the colorimetric mode light source between zero and the time of measurement, $c1$, may be expressed as follows:

$$c1 = \log 10((Dz*Rm)/(Dm*Rz)).$$

Figure 15:
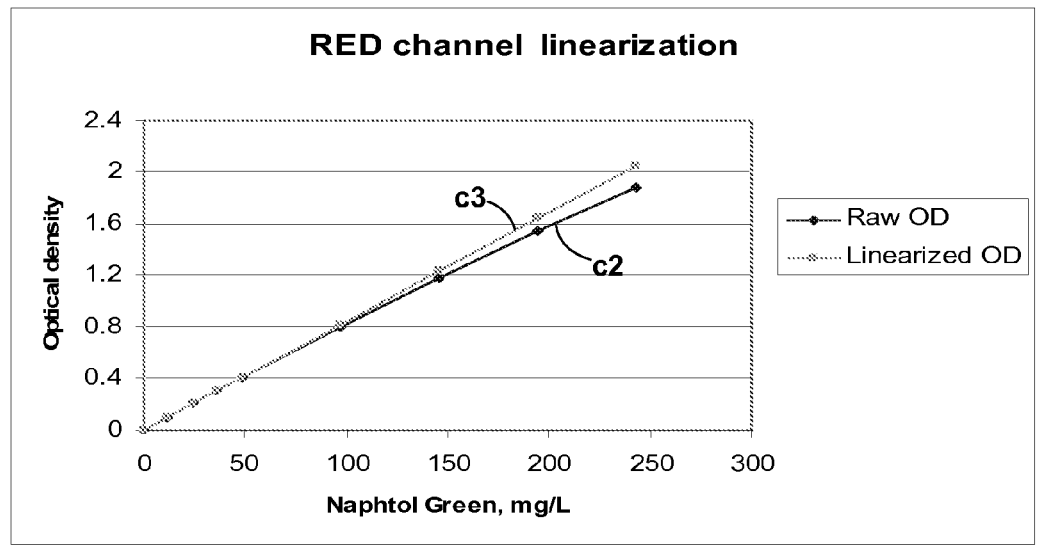
FIGS. 15-16 are graphs illustrating example linearization and normalization during processing for the red-red colorimetric channel.

Raw optical density $c1$ is then corrected for any color that may be present due to the reagent chemical compound. This results in a corrected raw optical density $c2$ according to the following equation:

$$c2 = c1 - RB,$$

where RB is the optical density due to the reagent chemical compound as measured previously (e.g., 120 in FIG. 11). An example of a corrected raw optical density curve $c2$ in the red-red colorimetric mode is shown in FIG. 15.

A linearization function is then applied to the corrected raw optical density, $c2$, to arrive at a linearized optical density, $c3$, as follows:

$$c3 = (c2*(R+c2*(S+c2*(V+U*c2)))),$$

where $c3$ results from applying the light source specific calibration curve. An example of a linearized optical density curve $c3$ in the red-red colorimetric mode is illustrated in FIG. 15. This calibration curve enables the optical density of Napthol Green B to correspond linearly to its concentration. The values of R, S, V and U are determined measuring several dye standards in ampoules and calculating coefficients to have minimal deviations from linearity.

Figure 16:
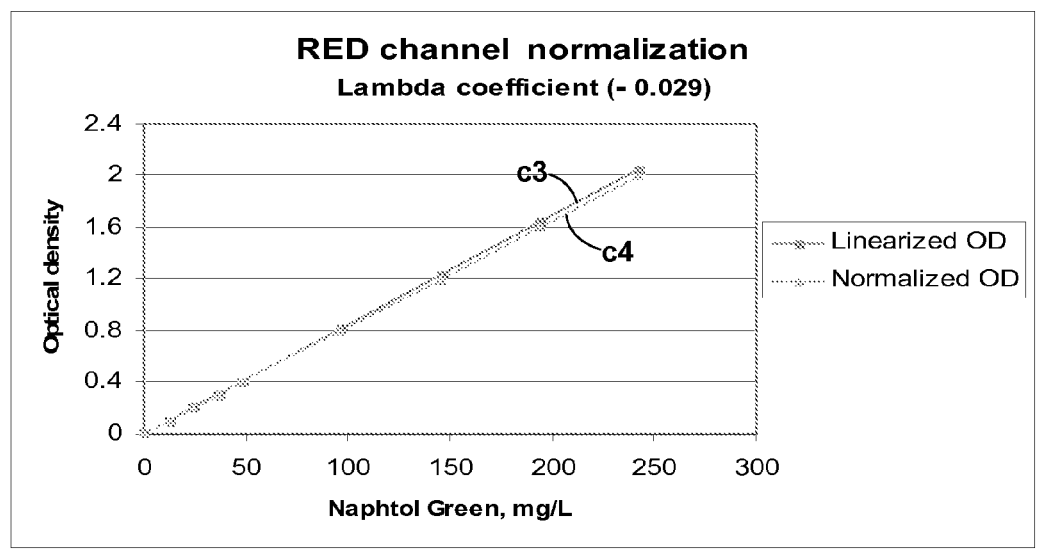

Next, a normalization function is applied to arrive at a normalized optical density, $c4$, as follows:

$c4 = c3*(1+(K*\text{Lambda}))$, where K equals 1 during calibration using dye standards. K is set in memory as an analyte specific coefficient to compensate for differences in optical properties of dye used for calibration and optical properties of colored chemical compound which is used for measuring of said analyte The colorimetric correction coefficient Lambda is unique to each multi-channel device 100 and to each colorimetric channel. The value of Lambda is chosen such that each device 100 reads a predefined optical density at a predefined concentration for a specific dye standard. For example, a dye standard correction coefficient Lambda may be calculated for each multi-channel device 100 such that each device 100 reads an optical density of 1.6000 at a nominal Napthol Green B dye concentration of 194.1 mg/L. An example of a linearized optical density curve, $c3$, and an example of a normalized optical density curve, $c4$, in the red-red colorimetric mode are illustrated in FIG. 16.

Because normalized optical density curve $c4$ for chosen dye is made linear, the analyte calibration curve $c5$ may be approximated with a single equation. The value of Thresh0 is therefore set such that only one range (range 0) is used in the calculation. Thus, normalized optical density curve $c4$ may be approximated by the following equation:

$$c5 = (A(Range0)*(E(Range0) + c4*(1.0 +$$
$$c4*(B(Range0) + c4*(C(Range0) + c4*D(Range0)))) +$$
$$K3(Range0)*(c4\textasciicircum(2*K4(Range0)))).$$

Next the end user calibration is applied such that $$c6 = \text{Alpha}*c5.$$

Finally the temperature correction may be applied resulting in $$c7 = c6*(1+K1*(tm-tc)+K2*((tm-tc)\textasciicircum2)).$$

The value $c7$ is the resulting analyte concentration.

Green-Green Colorimetric Mode

When measuring a photometric analyte using the green light source, the green-green colorimetric mode is selected and a set of constants are loaded from memory 31 as was described above with respect to the red-red colorimetric mode. However, the values of the constants are specific to the green-green colorimetric mode.

The direct (Dm) and reference (Rm) signal measurements are obtained and recorded. The optical density calculated from the measured values Dm and Rm is corrected for instability of the colorimetric mode light source (e.g., tri-color LED 59) using the Dz and Rz constants that were measured and stored before analysis of the unknown sample. For example, raw optical density corrected for instability of the colorimetric mode light source between zero and the time of measurement, $c1$, may be expressed as follows:

$$c1 = \log 10((Dz*Rm)/(Dm*Rz)).$$

Figure 17:
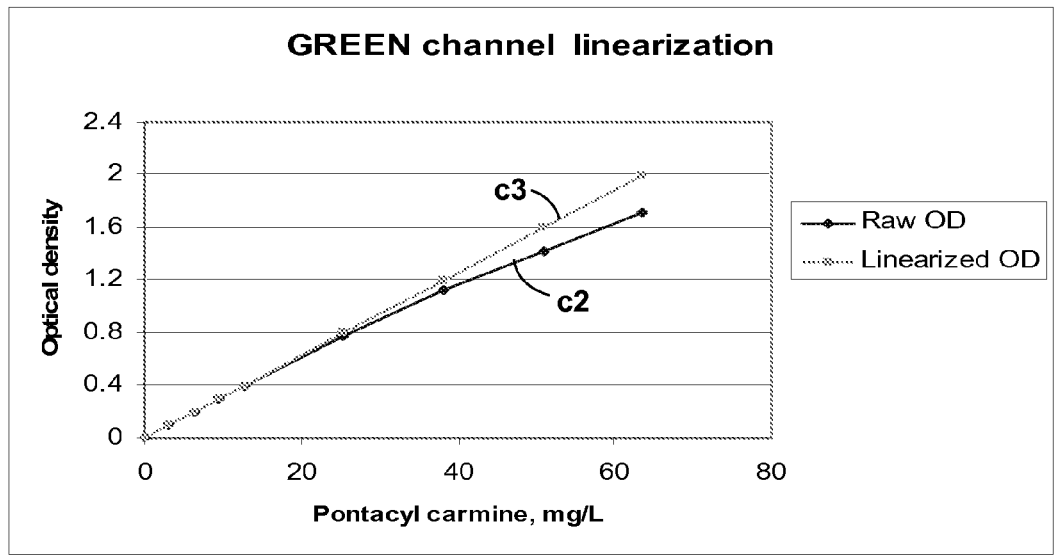
FIGS. 17-18 are graphs illustrating example linearization and normalization during processing for the green-green colorimetric channel.

Raw optical density $c1$ is then corrected for any color that may be present due to the reagent chemical compound. This results in a corrected raw optical density $c2$ according to the following equation:

$$c2 = c1 - RB,$$

where RB is the optical density due to the reagent chemical compound as measured previously (e.g., 120 in FIG. 11). An example of a corrected raw optical density curve $c2$ in the green-green colorimetric mode is shown in FIG. 17.

A linearization function is applied to the corrected raw optical density, $c2$, to arrive at a linearized optical density, $c3$, as follows:

$$c3 = (c2*(R+c2*(S+c2*(V+U*c2)))),$$

where $c3$ results from applying the light source specific calibration curve. An example of a linearized optical density curve $c3$ in the green-green colorimetric mode is illustrated in FIG. 17. The values of R, S, V and U similarly as described above for red-red colorimetric mode. This calibration curve enables the optical density of Pontacyl Carmine 2B to correspond linearly to its concentration.

Next, a normalization function is applied to arrive at a normalized optical density, $c4$, as follows:

$$c4 = c3*(1+(K*\text{Lambda})),$$

where K equals 1 during calibration using dye standards. K is set in memory as an analyte specific coefficient to compensate for differences in optical properties of dye used for calibration and optical properties of colored chemical compound which is used for measuring of said analyte.

Figure 18:
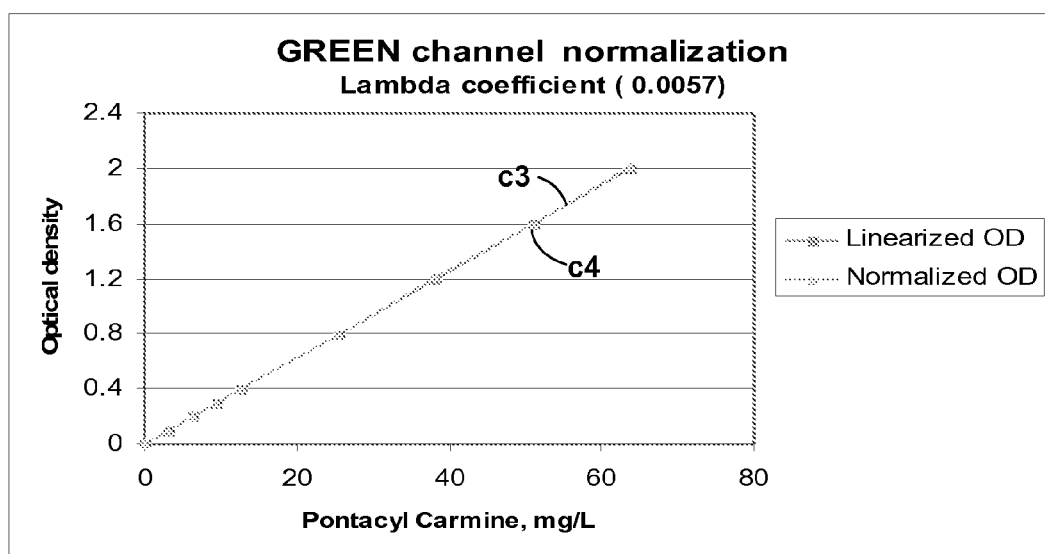

The colorimetric correction coefficient Lambda is unique to each multi-channel device 100 and to each colorimetric channel. The value of Lambda is chosen such that each device 100 reads a predefined optical density at a predefined concentration for a specific dye standard. For example, a colorimetric correction coefficient Lambda may be calculated for each multi-channel device 100 such that each device 100 reads an optical density of 1.6000 at a nominal Pontacyl Carmine 2B dye concentration of 50.9 mg/L. An example of a linearized optical density curve, $c3$, and an example of a normalized optical density curve, $c4$, in the green-green colorimetric mode are illustrated in FIG. 18.

Because normalized optical density curve c4 for chosen dye is made linear, the analyte calibration curve c5 may be approximated with a single equation. The value of Thresh0 is therefore set such that only one range (range 0) is used in the calculation. Thus, normalized optical density curve c4 may be approximated by the following equation:

$$c5 = (A(Range0)*(E(Range0) + c4*(1.0 + c4*(B(Range0) + c4*(C(Range0) + c4*D(Range0)))) + K3(Range0)*(c4\wedge(2*K4(Range0))))).$$

Next the end user calibration is applied such that $$c6 = Alpha*c5.$$

Finally the temperature correction may be applied resulting in $$c7 = c6*(1+K1*(tm-tc)+K2*((tm-tc)\wedge 2)).$$

The value c7 is the resulting analyte concentration.

Blue-Blue Colorimetric Mode

When measuring a photometric analyte using a blue light source and the a blue detector, the blue-blue colorimetric mode is selected and a set of constants are loaded from memory 31 as was described above with respect to the red-red colorimetric mode. However, the values of the constants are specific to the blue-blue colorimetric mode.

The direct (Dm) and reference (Rm) signal measurements are obtained and recorded. The optical density calculated from the measured values Dm and Rm is corrected for instability of the colorimetric mode light source (e.g., tri-color LED 59) using the Dz and Rz constants that were measured and stored before analysis of the unknown sample. For example, raw optical density corrected for instability of the colorimetric mode light source between zero and the time of measurement, c1, may be expressed as follows:

$$c1 = \log 10((Dz*Rm)/(Dm*Rz)).$$

Figure 19:
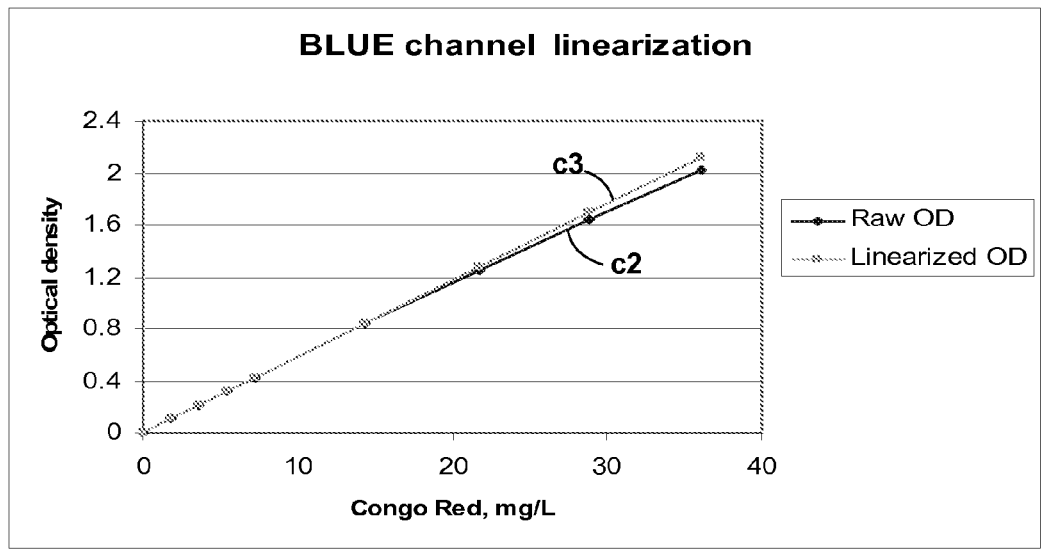
FIGS. 19-20 are graphs illustrating example linearization and normalization during processing for the blue-blue colorimetric channel.

Raw optical density c1 is then corrected for any color that may be present due to the reagent chemical compound. This results in a corrected raw optical density c2 according to the following equation:

$$c2 = c1 - RB,$$

where RB is the optical density due to the reagent chemical compound as measured previously (e.g., 120 in FIG. 11). An example of a corrected raw optical density curve c2 in the blue-blue colorimetric mode is shown in FIG. 19.

A linearization function is applied to the corrected raw optical density, c2, to arrive at a linearized optical density, c3, as follows:

$$c3 = (c2*(R+c2*(S+c2*(V+U*c2)))),$$

where c3 results from applying the light source specific calibration curve. An example of a linearized optical density curve c3 in the blue-blue colorimetric mode is illustrated in FIG. 19. The values of R, S, V and U similarly as described above for red-red and green-green colorimetric modes. This calibration curve enables the optical density of Congo Red to correspond linearly to its concentration.

Figure 20:
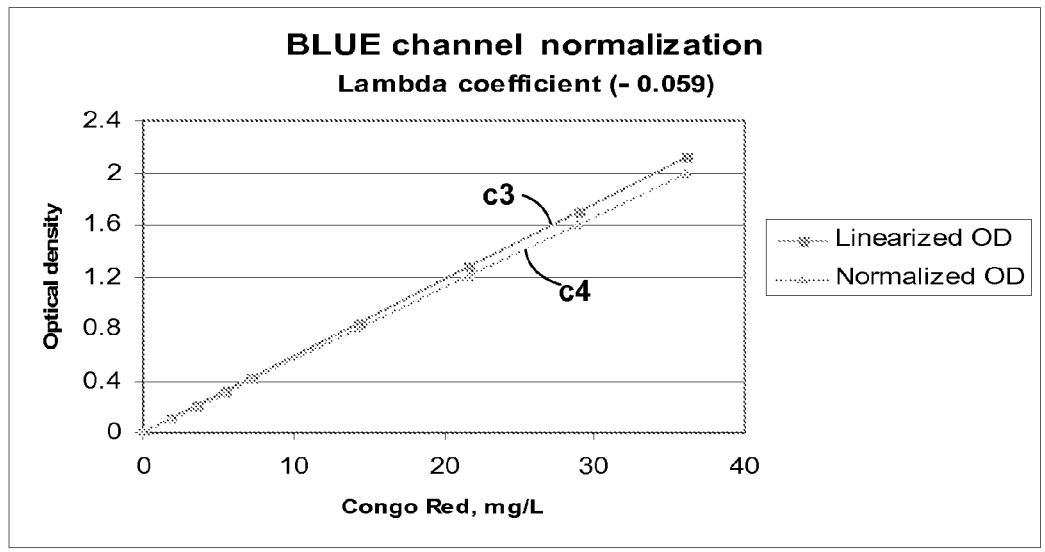

Next, a normalization function is applied to arrive at a normalized optical density, c4, as follows:

$$c4 = c3*(1+(K*Lambda)),$$

where K equals 1 during calibration using dye standards. K is set in memory as an analyte specific coefficient to compensate for differences in optical properties of dye used for calibration and optical properties of colored chemical compound which is used for measuring of said analyte The colorimetric correction coefficient Lambda is unique to each multi-channel device 100 and to each colorimetric channel. The value of Lambda is chosen such that each device 100 reads a predefined optical density at a predefined concentration for a specific dye standard. For example, a colorimetric correction coefficient Lambda may be calculated for each multi-channel device 100 such that each device 100 reads an optical density of 1.6000 at a nominal Congo Red dye concentration of 28.9 mg/L. An example of a linearized optical density curve, c3, and an example of a normalized optical density curve, c4, for the blue-blue colorimetric mode are illustrated in FIG. 20.

Because normalized optical density curve c4 for chosen dye is made linear, the analyte calibration curve c5 may be approximated with a single equation. The value of Thresh0 is therefore set such that only one range (range 0) is used in the calculation. Thus, normalized optical density curve c4 may be approximated by the following equation:

$$c5 = (A(Range0)*(E(Range0) + c4*(1.0 + c4*(B(Range0) + c4*(C(Range0) + c4*D(Range0)))) + K3(Range0)*(c4\wedge(2*K4(Range0))))).$$

Next the end user calibration is applied such that $$c6 = Alpha*c5.$$

Finally the temperature correction may be applied resulting in $$c7 = c6*(1+K1*(tm-tc)+K2*((tm-tc)\wedge 2)).$$

The value c7 is the resulting analyte concentration.

Mixed Colorimetric Mode(s)

Some analytes may be difficult to detect using a light source and a detector operating in the same wavelength range. For example, certain analytes together with chemistry developed for those analytes may result in an absorbance band shifted to the edges of the excitation range for any used light source. A detector centered on the same excitation wavelengths will receive a large signal when there is no analyte but will have a relatively smaller change of the transmitted signal when analyte is present. This may result in low accuracy of measurement. However, a detector centered on an adjacent wavelength range will receive a small signal when there is no analyte but will have a relatively larger change of the transmitted signal when an analyte is present. This may result in higher accuracy of measurement of optical density associated with the analyte concentration.

To help ensure detection of the transmitted signal in such cases and arrive at an accurate concentration of the target analyte, multi-channel device 100 may include at least one mixed colorimetric mode. In a mixed colorimetric mode, the wavelength ranges for the light source-detector combinations are adjacent rather than overlapping. To chose an optimal colorimetric mode from all available direct and mixed colorimetric modes one can use a spectral absorbance data for specific analyte and compare them with spectral data for light sources and detectors used in multi-channel device. The absorbance band for specific analyte can be shifted relative to maximum of spectral excitation range or covers several spectral excitation ranges. In this case measurements of optical densities for analyte should be made for direct and mixed colorimetric channels to find a channel where relative error for optical density measurements is minimal. This may help to ensure detection of specific analyte with better accuracy.

When using a tri-color RGB LED 59 and RGB detector 57 such as those shown in example multi-channel device 100 (see FIG. 7) there are four possible mixed colorimetric modes: a green-red colorimetric mode, a green-blue colorimetric mode, a red-green colorimetric mode and a blue-green colorimetric mode. The following is a description of the processing for the green-red colorimetric mode. However, it shall be understood that the processing for each of the mixed colorimetric modes would be similar to that described with respect to the green-red colorimetric mode.

The green-red colorimetric modes may be useful for measurement of analytes such as fluoride, bromine, cyanide, etc.

For example, when measuring a photometric analyte that uses green light source and a red detector the following procedure is performed. First an ampoule to be read is placed in the chamber. Next the unit is placed in the Green-Red colorimetric mode. This results in the loading of lightsource, equation, Dz, Sz, Rz, RB, R, S, U, V, Lambda, K, N, A(Range0), B(Range0), C(Range0), D(Range0), E(Range0), K3(Range0), K4(Range0), A(Range1), B(Range1), C(Range1), D(Range1), E(Range1), K3(Range1), K4(Range1), A(Range2), B(Range2), C(Range2), D(Range2), E(Range2), K3(Range2), K4(Range2), K1, K2, Alpha, Thresh0, Thresh1 and tc calibration coefficients. The direct (Dm) and reference (Rm) signal measurements are obtained and recorded.

The optical density calculated from the measured values Dm and Rm is corrected for instability of the colorimetric mode light source (e.g., tri-color LED 59) using the Dz and Rz constants that were measured and stored before analysis of the unknown sample. For example, raw optical density corrected for instability of the colorimetric mode light source between zero and the time of measurement, $c_1$, may be expressed as follows:

$$c_1 = \log 10((Dz*Rm)/(Dm*Rz)).$$

Figure 21:
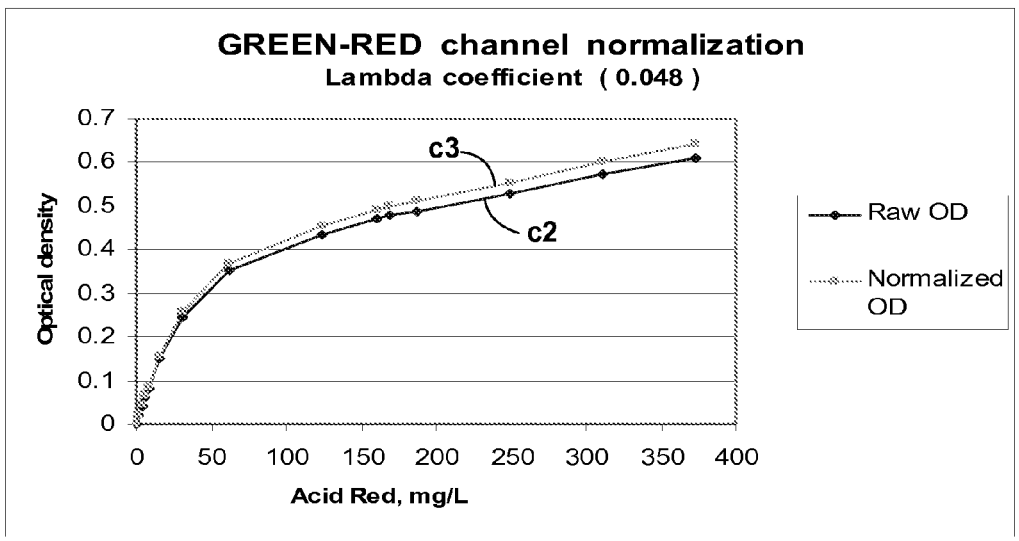
FIG. 21 is a graph illustrating example normalization during processing for the green-red colorimetric channel.

Raw optical density $c_1$ is then corrected for any color that may be present due to the reagent chemical compound. This results in a corrected raw optical density $c_2$ according to the following equation:

$$c_2 = c_1 - RB.$$

where RB is the optical density due to the reagent chemical compound as measured previously (e.g., 120 in FIG. 11). An example of a corrected raw optical density curve $c_2$ in the green-red colorimetric mode is shown in FIG. 21.

A normalization function is then applied to the corrected raw optical density, $c_2$, to arrive at a normalized optical density, $c_3$, as follows:

$$c_3 = (R*c_2),$$

where R is found from forcing the $c_3$ to be equal 0.5 when reading 169.1 mg/L of Acid Red 183 relative to a local blank. An example of a normalized optical density curve $c_3$ in the green-red colorimetric mode is shown in FIG. 21. Because only coefficient R applied to scale $c_2$ the normalized curve for optical density stays nonlinear. The Green-Red channel was optimized for measuring of fluoride, where it is important to have linearity at the high absorbance (for optical density from 0.4 to 0.8). There are some differences between Green-Red channel and other colorimetric channels. It has no Lambda correction and no K as analyte specific correction coefficients.

When the Green-Red colorimetric channel is used for specific analytes, three ranges may be used for linearization could be needed for calibration curve as described above. Now the analyte calibration is applied.

It then follows if $c_3 < Thresh0$ that $$c_5 = (A(Range0)*(E(Range0) + c_3*(1.0 + c_3*(B(Range0) + c_3*(C(Range0) + c_3*D(Range0)))) + K3(Range0)*(c_3^{(2*K4(Range0))}))).$$

Otherwise if $c_3 < Thresh1$ it then follows that $$c_5 = (A(Range1)*(E(Range1) + c_3*(1.0 + c_3*(B(Range1) + c_3*(C(Range1) + c_3*D(Range1)))) + K3(Range1)*(c_3^{(2*K4(Range1))}))).$$

If the two previous conditions are not met, it then follows that $$c_5 = (A(Range2)*(E(Range2) + c_3*(1.0 + c_3*(B(Range2) + c_3*(C(Range2) + c_3*D(Range2)))) + K3(Range2)*(c_3^{(2*K4(Range2))}))).$$

Next the end user calibration is applied such that $$c_6 = Alpha*c_5.$$

Finally the temperature correction may be applied resulting in $$c_7 = c_6*(1 + K1*(tm-tc) + 1K2*((tm-tc)^2)).$$

The value $c_7$ is the resulting analyte concentration.

Fluoride Channel

When measuring the concentration of fluoride in a liquid sample the following procedure is performed. First an ampoule to be read is placed in the chamber. Next the unit is placed in the Green-Red photometric mode. This results in the loading of lightsource, equation, Dz, Sz, Rz, RB, R, Lambda, K, N, A(Range0), B(Range0), C(Range0), D(Range0), E(Range0), K3(Range0), K4(Range0), A(Range1), B(Range1), C(Range1), D(Range1), E(Range1), K3(Range1), K4(Range1), A(Range2), B(Range2), C(Range2), D(Range2), E(Range2), K3(Range2), K4(Range2), K1, K2, Alpha, Thresh0, Thresh1 and tc calibration coefficients. Next, a measurement is taken. The values Dm, Sm and Rm are recorded.

The optical density calculated from the measured values Dm and Rm is corrected for instability of the Fluoride channel light source (e.g., tri-color LED 59) using the Dz and Rz constants that were measured and stored before analysis of the unknown sample. For example, raw optical density corrected for instability of the colorimetric mode light source between zero and the time of measurement, $c_1$, may be expressed as follows:

$$c_1 = \log 10((Dz*Rm)/(Dm*Rz))$$

Figure 22:
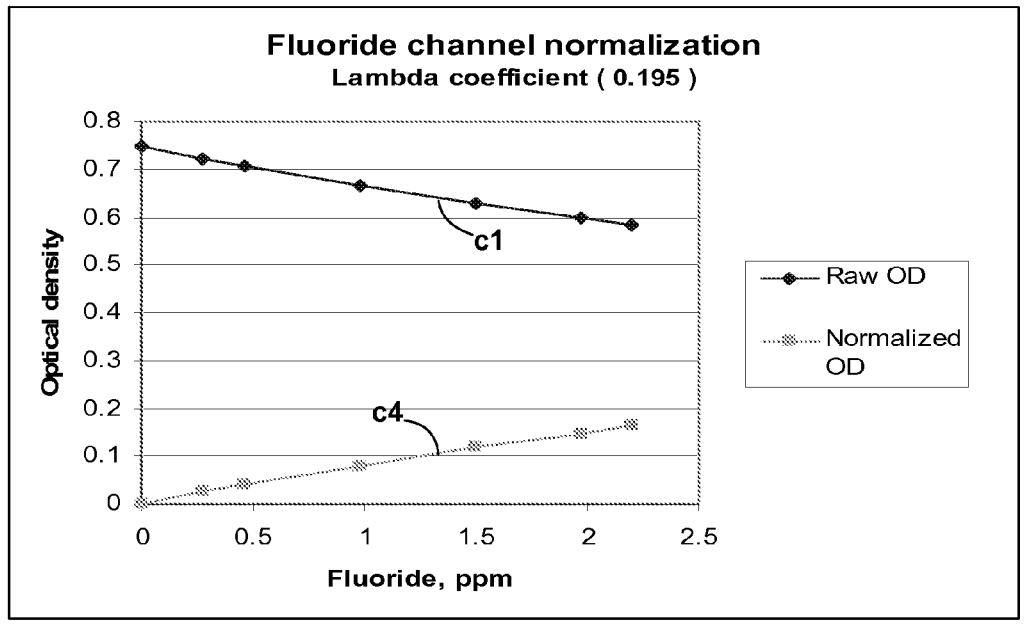
FIG. 22 is a graph illustrating example normalization during processing for the fluoride colorimetric channel.

An example raw optical density curve c1 in the fluoride colorimetric mode is shown in FIG. 22.

Raw optical density c1 is then corrected for absorbance of the reagent chemical compound using a reagent blank. The corrected raw optical density c2 is determined according to the following equation:

$$c2 = c1 - RB,$$

where RB is the optical density due to the reagent chemical compound as measured previously (e.g., 120 in FIG. 11).

A normalization function is then applied to the corrected raw optical density, c2, to arrive at a normalized optical density, c3, as follows:

$$c3 = (R * c2),$$

where R results from Green-Red channel normalization forcing the signal for c3 to be equal 0.5 when reading 169.1 mg/L of Acid Red 183 relative to a local blank. Next, $$c4 = c3 * N * (1 + Lambda),$$

where Lambda is a correction coefficient such that c4 is equal to 0.147.

Because the raw optical density curve c1 has a negative slope (due to the fact that the sample bleaches when mixed with the reagent rather than turning a darker color) the value N is set to −1 for the fluoride channel. This results in the normalized optical density c4 having a positive slope as illustrated in the example normalized optical density curve c4 for the fluoride channel as shown in FIG. 22.

K equals 1 during calibration using dye standards. K is set in memory as an analyte specific coefficient to compensate for differences in optical properties of dye used for calibration and optical properties of colored chemical compound which is used for measuring of said analyte. The colorimetric correction coefficient Lambda is unique to each multichannel device 100 and to each colorimetric channel. The value of Lambda is chosen such that each device 100 reads a predefined optical density at a predefined concentration for a specific dye standard.

Because normalized optical density curve c4 for fluoride is almost linear (see FIG. 22), the fluoride calibration curve c5 may be approximated with a single equation. The value of Thresh0 is therefore set such that only one range (range 0) is used in the calculation. Thus, normalized optical density curve c4 may be approximated by the following equation:

$$c5 = (A(Range0) * (E(Range0) + c3 * (1.0 +$$
$$c3 * (B(Range0) + c3 * (C(Range0) + c3 * D(Range0)))) +$$
$$K3(Range0) * (c3 \wedge (2 * K4(Range0)))).$$

Next the end user calibration is applied such that $$c6 = Alpha * c5.$$

Finally the temperature correction may be applied resulting in $$c7 = c6 * (1 + K1 * (tm - tc) + K2 * ((tm - tc)\hat{} 2)).$$

The value c7 is the resulting analyte concentration.

The following table lists multiple analytes along with example corresponding ranges of concentrations and light source-detector channel combinations.

|    | Analyte    | Range of concentrations | Light source-Detector Channel |
|----|------------|-------------------------|-------------------------------|
| 1  | Molibdate  | 0-25 mg/L               | UV-UV                         |
| 2  | Phosphate  | 0-40 mg/L               | UV-UV                         |
| 3  | Silica     | 0-10 mg/L               | Red-Red                       |
| 4  | Ozone      | 0-3 mg/L                | Red-Red                       |
| 5  | Zinc       | 0-3 mg/L                | Red-Red                       |
| 6  | Sulfide    | 0-3 mg/L                | Red-Red                       |
| 7  | Nitrite    | 0-0.8 mg/L              | Green-Green                   |
| 8  | Chlorine   | 0-5 mg/L                | Green-Green                   |
| 9  | Iron       | 0-6 mg/L                | Green-Green                   |
| 10 | Nitrate    | 0-1 mg/L                | Green-Green                   |
| 11 | Manganese  | 0-30 mg/L               | Green-Green                   |
| 12 | Chloride   | 0-40 mg/L               | Blue-Blue                     |
| 13 | Copper     | 0-40 mg/L               | Blue-Blue                     |
| 14 | Fluoride   | 0-2 mg/L                | Green-Red                     |
| 15 | Bromine    | 0-9 mg/L                | Green-Red                     |
| 16 | Cyanide    | 0-0.4 mg/L              | Green-Red                     |

Various embodiments of the invention have been described. These and other embodiments are within the scope of the following claims.

The invention claimed is:

1. An apparatus comprising:
   a sample chamber that holds a liquid sample of which at least one analyte concentration is to be determined;
   a single axis colorimetric channel configured to provide a red-red colorimetric mode, a blue-blue colorimetric mode, a green-green colorimetric mode, and at least one mixed colorimetric mode, wherein the colorimetric channel further includes:
      a multicolor light source controllable to emit light of a selected one of a red wavelength range, a blue wavelength range, and a green wavelength range into the liquid sample; and
      a multicolor detector arranged opposite the sample chamber from the multicolor light source and controllable to detect light of the selected one of the red wavelength range, the blue wavelength range, or the green wavelength range transmitted through the liquid sample; and
   a controller that is configured to selectively control which one of the red wavelength range, the blue wavelength range, or the green wavelength range is emitted by the multicolor light source, selectively controls which one of the red wavelength range, the blue wavelength range, or the green wavelength range p is detected by the multicolor detector, and determines the at least one analyte concentration of the liquid sample based on at least the selected one of the red wavelength range, the blue wavelength range, or the green wavelength range detected by the multicolor detector,
   wherein in a first mixed colorimetric mode the controller further controls the multicolor light source to emit light in the green wavelength range and controls the multicolor detector to detect light in the red wavelength range,
   wherein in a second mixed colorimetric mode the controller further controls the multicolor light source to emit light in the green wavelength range and controls the multicolor detector to detect light in the blue wavelength range,
   wherein in a third mixed colorimetric mode the controller further controls the multicolor light source to emit light in the red wavelength range and controls the multicolor detector to detect light in the green wavelength range,
   wherein in a fourth mixed colorimetric mode the controller further controls the multicolor light source to emit light in the blue wavelength range and controls the multicolor detector to detect light in the green wavelength range.

2. The apparatus of claim 1 wherein the multicolor light source is a tri-color LED (light emitting diode).

3. The apparatus of claim 1 further comprising an ampoule,
wherein the sample chamber is sized to receive the ampoule containing the liquid sample, and
wherein the sample chamber contains water during determination of the at least one analyte concentration such that the water surrounds the ampoule in the sample chamber during determination of the at least one analyte concentration.

4. The apparatus of claim 1 wherein the liquid sample includes at least one of free chlorine, total chlorine, copper, phosphate and fluoride.

5. The apparatus of claim 1, further comprising:
a turbidity channel configured to provide a turbidity mode, wherein the turbidity channel further includes:
a first light source controllable to emit light into the sample chamber; and
a first detector arranged opposite the sample chamber from the first light source and controllable to detect light emitted by the first light source transmitted through the liquid sample; and
a color channel configured to provide a color mode, wherein the color channel further includes:
a second light source controllable to emit light into the sample chamber; and
a second detector arranged opposite the sample chamber from the second light source and controllable to detect light emitted by the second light source transmitted through the liquid sample in the color mode, and to detect scattered light emitted by the first light source transmitted through the liquid sample in the turbidity mode;
wherein the single axis colorimetric channel, the turbidity channel, and the color channel are symmetrically arranged in a plane perpendicular to a z-axis of the sample chamber;
wherein the controller determines a turbidity of the water sample based on the transmitted light detected by the first detector and the scattered light detected by the second detector when in the turbidity mode, and determines a color of the water sample based on the transmitted light detected by the second detector when in the color mode.

6. An apparatus comprising:
an ampoule containing a liquid sample of which at least one analyte concentration is to be determined;
a sample chamber sized to receive the ampoule containing a liquid sample of which at least one analyte concentration is to be determined;
a single axis colorimetric channel that measures the at least one analyte concentration of the liquid sample, the colorimetric channel configured to provide a red-red colorimetric mode, a blue-blue colorimetric mode, a green-green colorimetric mode, and at least one mixed colorimetric mode, wherein the colorimetric channel further includes:
a multicolor light source controllable to emit light of a selected one of a red wavelength range, a blue wavelength range, and a green wavelength range into the liquid sample; and
a multicolor detector arranged opposite the sample chamber from the multicolor light source and controllable to detect light of the selected one of the of the red wavelength range, the blue wavelength range, or the green wavelength range transmitted through the liquid sample; and
a controller that is configured to selectively control which of the of the red wavelength range, the blue wavelength range, or the green wavelength range is emitted by the multicolor light source, selectively controls which of the of the red wavelength range, the blue wavelength range, or the green wavelength range is detected by the multicolor detector, and determines the at least one analyte concentration of the liquid sample based on at least the selected one of the of the red wavelength range, the blue wavelength range, or the green wavelength range detected by the multicolor detector,
wherein the sample chamber contains water that surrounds the ampoule in the sample chamber during determination of the at least one analyte concentration,
wherein in a first mixed colorimetric mode the controller further controls the multicolor light source to emit light in the green wavelength range and controls the multicolor detector to detect light in the red wavelength range,
wherein in a second mixed colorimetric mode the controller further controls the multicolor light source to emit light in the green wavelength range and controls the multicolor detector to detect light in the blue wavelength range,
wherein in a third mixed colorimetric mode the controller further controls the multicolor light source to emit light in the red wavelength range and controls the multicolor detector to detect light in the green wavelength range, and
wherein in a fourth mixed colorimetric mode the controller further controls the multicolor light source to emit light in the blue wavelength range and controls the multicolor detector to detect light in the green wavelength range.

7. An apparatus comprising:
a sample chamber that holds a liquid sample of which at least one analyte concentration is to be determined;
a single axis colorimetric channel that measures the at least one analyte concentration of the liquid sample, wherein the colorimetric channel further includes:
a multicolor light source controllable to emit light having one of a red wavelength range, a green wavelength range, or a blue wavelength range;
at least one excitation-side focusing optical component that directs the light emitted by the multicolor light source through the sample chamber;
a multicolor detector controllable to detect light having one of the red wavelength range, the green wavelength range, or the blue wavelength range transmitted through the liquid sample; and
at least one emission-side focusing optical component that directs light transmitted through the sample chamber onto the multicolor detector; and
a controller that is configured to determine the at least one analyte concentration of the liquid sample based on the selected one of the red wavelength range, the green wavelength range, or the blue wavelength range detected by the multicolor detector,
wherein in a first mixed colorimetric mode the controller further controls the multicolor light source to emit light in the green wavelength range and controls the multicolor detector to detect light in the red wavelength range, wherein in a second mixed colorimetric mode the controller further controls the multicolor light source to emit light in the green wavelength range and controls the multicolor detector to detect light in the blue wavelength range, wherein in a third mixed colorimetric mode the controller further controls the multicolor light source to emit light in the red wavelength range and controls the multicolor detector to detect light in the green wavelength range, wherein in a fourth mixed colorimetric mode the controller further controls the multicolor light source to emit light in the blue wavelength range and controls the multicolor detector to detect light in the green wavelength range.

8. The apparatus of claim 7 wherein the at least one excitation-side focusing optical component includes one or more positive lenses and the at least one emission-side focusing optical component includes a positive lens and a ball lens.

9. The apparatus of claim 7 wherein the multicolor light source is a tri-color LED (light emitting diode).

10. An apparatus comprising:
a sample chamber that holds a liquid sample of which at least one analyte concentration is to be determined;
a single axis colorimetric channel configured to provide at least one mixed colorimetric mode, wherein the single axis colorimetric channel further includes:
a multicolor light source controllable to emit light of a selected one of a red wavelength range, a blue wavelength range, and a green wavelength range into the liquid sample; and
a multicolor detector arranged on the single axis opposite the sample chamber from the multicolor light source and controllable to detect light of a selected one of the red wavelength range, the blue wavelength range, or the green wavelength range transmitted through the liquid sample that is different than the selected one of the red wavelength range, the blue wavelength range, and the green wavelength range emitted by the multicolor light source; and
a controller that, in the at least one mixed colorimetric mode, is configured to selectively control which one of the red wavelength range, the blue wavelength range, or the green wavelength range is emitted by the multicolor light source, selectively controls which one of the red wavelength range, the blue wavelength range, or the green wavelength range is detected by the multicolor detector, and determines the at least one analyte concentration of the liquid sample based on at least the selected one of the red wavelength range, the blue wavelength range, or the green wavelength range detected by the multicolor detector.

* * * * *